United States Patent
Nakamura et al.

(10) Patent No.: US 7,549,750 B2
(45) Date of Patent: Jun. 23, 2009

(54) OPTOMETER

(75) Inventors: Shinichi Nakamura, Tokyo (JP); Hiroaki Ogushi, Tokyo (JP)

(73) Assignee: Kabushiki Kaisha Topcon, Itabashi-Ku (JP)

( * ) Notice: Subject to any disclaimer, the term of this patent is extended or adjusted under 35 U.S.C. 154(b) by 154 days.

(21) Appl. No.: 11/218,766

(22) Filed: Sep. 6, 2005

(65) Prior Publication Data

US 2006/0050238 A1 Mar. 9, 2006

(30) Foreign Application Priority Data

Sep. 6, 2004 (JP) .............................. 2004-257984

(51) Int. Cl.
*A61B 3/02* (2006.01)

(52) U.S. Cl. ..................................... 351/237

(58) Field of Classification Search .......... 351/200–247
See application file for complete search history.

(56) References Cited

U.S. PATENT DOCUMENTS

| | | | | |
|---|---|---|---|---|
| 5,325,136 A | * | 6/1994 | Salibello et al. | 351/243 |
| 5,502,519 A | * | 3/1996 | Hosoi | 351/204 |
| 2002/0024633 A1 | * | 2/2002 | Kim et al. | 351/206 |
| 2002/0047987 A1 | * | 4/2002 | Massengill et al. | 351/204 |
| 2003/0081175 A1 | * | 5/2003 | Hosoi et al. | 351/222 |
| 2003/0174282 A1 | * | 9/2003 | Itagaki | 351/200 |
| 2004/0032568 A1 | * | 2/2004 | Fukuma et al. | 351/233 |
| 2005/0041210 A1 | * | 2/2005 | Isogai et al. | 351/205 |
| 2005/0122475 A1 | * | 6/2005 | Vilser et al. | 351/221 |
| 2006/0023163 A1 | * | 2/2006 | Foster | 351/246 |

FOREIGN PATENT DOCUMENTS

| | | |
|---|---|---|
| JP | 2002-315723 | 10/2002 |
| JP | 2004-045215 | 2/2004 |

* cited by examiner

*Primary Examiner*—Jessica T Stultz
*Assistant Examiner*—Mahidere S Sahle
(74) *Attorney, Agent, or Firm*—Edwards Angell Palmer & Dodge LLP

(57) ABSTRACT

An optometer capable of recording an examination result without making an error even in a case of using an apparatus with a structure to mechanically display the examination result. The optometer includes a phoropter (120), an imaging device (2) for taking an image of the phoropter (120), the image including a display portion of the phoropter (120), a display position specifying portion (135*b*) for analyzing the taken image and specifying a position of the display portion in the taken image, a display content acquisition portion (135*c*) for acquiring display contents (examination results) of the display portion whose position is specified, and a display control portion (135*d*) for displaying the acquired examination results on a monitor portion (131). The display portion includes a PD display portion (122), a spherical power display portion (161), a spherical power display portion (162), a cylindrical axis display portion (164), and a rotary prism portion (155).

14 Claims, 13 Drawing Sheets

OPTOMETER

BACKGROUND OF THE INVENTION

1. Field of the Invention

The present invention relates to an optometer for performing a refraction measurement of eyes to be examined, and more particularly to a technology for automatically inputting characters and symbols, which represent measurement values of a refractive power, an inter-pupil distance, and the like displayed on the optometer.

2. Description of the Related Art

In recent years, networking and automation of an optometer for use in an eyeglass shop have been progressing. However, for a phoropter, a trial frame, and the like, manual types, that is, manually operated types have been mainstreams because of merits in terms of operability, cost, and the like (for example, refer to JP 2002-315723 A, Paragraph Nos. 0007 and 0008 in Specification, and FIG. 1).

FIG. 11 shows an example of a conventional optometer. An optometer 100 shown in the drawing is a system for performing a subjective measurement of eyes to be examined. The optometer 100 has a structure including a manual-type subjective optometer (phoropter) 120 suspending above a table 101 with a column 102 and first and second arms 103 and 104 interposed therebetween, a computer device 130 disposed on the table 101, and an optotype device 140 arranged to be spaced apart from the phoropter 120 by a predetermined distance (distance-sight measurement distance: 3 meters, 5 meters, etc.). Note that an objective optometer (refractometer) may be provided together with the phoropter 120. Further, beside the table 101, a chair (not shown) is provided, and a subject takes an examination while sitting on the chair.

The computer device 130 includes a monitor portion 131 such as a liquid crystal display, and input portions such as a keyboard 132 and a mouse 133 for use in input operations for designating various operations of the optometer 100. On the monitor portion 131, a variety of operation screens, measurement result display screens, and the like are displayed.

Further, the optotype device 140 displays a distance optometry target (chart) C such as a Landolt ring on a presentation window 141, and presents the target C to the subject. The target C presented to the subject is selected by the mouse 133 and the like based on the operation screen displayed on the monitor portion 131 of the computer device 130.

FIG. 12 shows a structure of a front face (face opposite to the optotype device 140) of the phoropter 120. The phoropter 120 includes a right measurement unit 120R for performing a refraction measurement for a right eye to be examined, a left measurement unit 120L for performing a refraction measurement for a left eye to be examined, and a support unit 120A for supporting these measurement units 120R and 120L.

The right measurement unit 120R and the left measurement unit 120L are composed to be left-and-right symmetric. In the drawing, detailed description of the left measurement unit 120L is omitted. Description is made below only of a structure of the right measurement unit 120R (hereinafter, sometimes simply referred to as a "measurement unit 120R").

The support unit 120A supports the respective measurement units 120R and 120L so that the measurement units 120R and 120L can be individually displaced in a left-and-right direction. On side surfaces of the support unit 120A, PD change knobs 121 for displacing the respective measurement units 120R and 120L to the left and the right are provided. An examiner rotationally operates the PD change knobs 121, and arranges optometric windows 150 of the respective measurement units 120R and 120L immediately in front of the right eye to be examined and the left eye to be examined. Specifically, the PD change knobs 121 are operated to align a width between the left and right optometric windows 150 with the inter-pupil distance (PD) of the subject. The width between the left and right optometric windows 150 (between optical axes of lenses arranged therein) is displayed on a PD display portion 122.

Further, the support unit 120A supports a forehead rest 123 disposed on back sides of the right measurement unit 120R and the left measurement unit 120L. Reference numeral 124 denotes an indicator representing a contact pressure of the forehead of the subject to the forehead rest 123. Further, provided on an upper center portion of the support unit 120A is a near-optometric rod attachment portion 125 onto which a rod for supporting a target for a near-distance test of the eyes to be examined is attached. The near-optometric rod attachment portion 125 is set to be rotatable between a vertically upper direction and a horizontally forward direction, is inclined to the horizontally forward direction to present the near optometric target to the eyes to be examined at the time of the near optometric test, and is received in the vertically upper direction at the time of being unused.

In the measurement unit 120R, various optometric lenses including correction lenses such as a group of spherical lenses for correcting a spherical power of the eye to be examined and a group of cylindrical lenses for correcting a cylindrical power thereof are incorporated. The respective optometric lenses are provided on a turret plate and the like so as to be selectively disposed on the optometric window 150 of the measurement unit 120R. The right eye to be examined peers through the optometric window 150 from the back side of the measurement unit 120R, thereby visually recognizing the target C presented to the optotype device 140.

Description is further made of a structure of the front face of the right measurement unit 120R with reference to FIGS. 13 to 15.

Provided on the front face of the measurement unit 120R are a spherical power changing portion 151 for changing a spherical power (correcting a spherical power) of correcting the eye to be examined, that is, for changing the spherical lens disposed on the optometric window 150, and a spherical power display portion 161 for mechanically displaying the spherical power of the spherical lens disposed on the optometric window 150.

The spherical power changing portion 151 has a structure including a first change knob 151a rotationally operated in order to change the correcting spherical power stepwise by each (±) 0.25 diopters, and a second change knob 151b formed to protrude to a center portion of the first change knob 151a and for changing the correcting spherical power stepwise by each (±) 3 diopters.

The spherical power display portion 161 changes the spherical power displayed thereon in correspondence with rotation of the spherical power changing portion 151. More specifically, when the first change knob 151a is rotated by one step, a numeric value displayed on the spherical value display portion 161 is changed by "(+/−) 0.25" in response to a direction of the rotation. In a similar way, when the second change knob 151b is rotated by one step, a numeric value displayed on the spherical value display portion 161 is changed by "(+/−) 3" in response to a direction of the rotation. Such a corresponding operation of the change and display of the spherical power is performed by an interlocking mechanism in the measurement unit 120R.

Further, provided in the measurement unit 120R is a cylindrical power changing portion 152 for changing the cylindrical power (correcting the cylindrical power) of correcting the eye to be examined, that is, for changing the cylindrical lens disposed on the optometric window 150, and a cylindrical power display portion 162 for mechanically displaying the cylindrical power of the cylindrical lens disposed on the optometric window 150.

When the cylindrical power changing portion 152 is rotated by one step, the correcting cylindrical power is changed by (±) 0.25 diopters in response to a direction of the rotation. When the cylindrical power changing portion 152 is rotated by one step, a numeric value displayed on the cylindrical power display portion 162 is changed by "(+/−) 0.25" in response to the direction of the rotation. This corresponding operation is also performed by the corresponding mechanism in the measurement unit 120R.

Further, a lens support plate 153 rotatable about a shaft 153a is attached onto the front face of the measurement unit 120R. Provided on both ends of the lens support plate 153 are a cross cylinder lens portion 154 for a cross cylinder test, and a rotary prism portion 155 for prism examination, which are for examining astigmatism of the eye to be examined. A cylindrical axis display portion 164 for displaying a cylindrical axis degree in the cross cylinder test is provided around the shaft 153a of the lens support plate 153. Further, an operation knob 153b is formed at one end of the lens support plate 153. The examiner rotates the lens support plate 153 by holding the operation knob 153b, thus making it possible to dispose the cross cylinder portion 154 or the rotary prism portion 155 immediately in front of the optometric window 150.

The cross cylinder lens portion 154 includes a cylindrical lens 154a in a center portion thereof. The cylindrical lens 154a is structured so that a front and back thereof can be switched about, as a center, a rotation axis inclined by 45° with respect to a cylindrical axis thereof. The switching of the front and back of the cylindrical lens 154a is performed by rotating a switch dial 154b.

Further, the cross cylinder lens portion 154 is structured to be rotatable about an optical axis of the cylindrical lens 154a as a center, thus making it possible to change the cylindrical axis degree of the cylindrical lens 154a. The cylindrical axis degree of the cylindrical lens 154a is displayed on the cylindrical axis display portion 164.

As shown in FIG. 14, the cylindrical axis display portion 164 includes a mechanical structure including a disc-like dial plate 164a in which a scale representing the cylindrical axis degree is written on a peripheral edge portion, and indication marks 164c provided on an edge end portion 164b on the periphery of the dial plate 164a and for indicating the scale on the dial plate 164a. On the scale on the dial plate 164a, the cylindrical axis degrees of 0° to 180° are written twice. The indication marks 164c are provided in a pair at positions opposite to each other with the dial plate 164a interposed therebetween (that is, positions apart from each other by 180°). The indication marks 164c individually indicate scales of the same frequency as that of the dial plate 164a.

The dial plate 164a is structured so as not to rotate together with the lens support plate 153 or the cross cylinder lens portion 154 even if either thereof is rotated (in the dial plate 164a of FIG. 14, a line of 0° to 180° is always located horizontally). Meanwhile, the edge end portion 164b is structured so as, when the cross cylinder lens portion 154 is rotated, to rotate about the shaft 153a as a center by the same degree as a displacement of the cylindrical axis degree of the cylindrical lens 154a in correspondence with the rotation of the cross cylinder lens portion 154 though not to rotate even if the lens support plate 153 is rotated. In such a way, the indication marks 164c indicate the scales equal to the cylindrical axis degree of the cylindrical lens 154a. Note that the corresponding operation of the rotation of the edge end portion 164b with the rotation of the cross cylinder lens portion 154 is performed by the interlocking mechanism in the measurement unit 120R.

As shown in FIG. 15, the rotary prism portion 155 includes a mechanical structure including a prism portion 155a including two lenses for generating a prism power, a holding portion 155b for holding the two lenses of the prism portion 155a, an indication mark 155c provided on the holding portion 155b, an annular dial plate 155d on which a scale representing the prism power is provided, and a change dial 155e for changing the prism power generated by the prism portion 155a by rotating the respective lenses thereof.

The rotary prism portion 155 is structured so as not to rotate even if the lens support plate 153 is rotated. Further, the dial plate 155d is structured so as not to rotate even if the change dial 155e is rotationally operated. In the dial plate 155d of FIG. 15, a line of "20" to "20" is always located vertically.

The two lenses of the prism portion 155a individually have a prism power of, for example, 10 prism diopters. The lenses concerned are rotated in response to an operation to the change dial 155e, thus making it possible for the prism portion 155a to generate a prism power of 0 to 20 prism diopters. Further, these two lenses are rotated together, thus making it possible to change a prism base direction. On the dial plate 155d, a scale is provided within the range of 0 to 20 prism diopters in response to the prism base direction (of raising and lowering the base).

When the change dial 155e is rotated, the holding portion 155b is rotated together with the lenses of the prism portion 155a (the dial plate 155d is not rotated). At this time, the indication mark 155c on the holding portion 155b is also rotated, and indicates the scale on the dial plate 155d, which represents the prism power generated by the prism portion 155a.

Further, provided on the front face of the measurement unit 120R is an auxiliary lens switching portion 156 for selectively disposing auxiliary optometric lenses such as various auxiliary lenses in the optometric window 150. Usable as the auxiliary optometric lenses applied in a switching manner by the auxiliary lens switching portion 156 are, for example, a spherical lens, a cylindrical lens, a prism, a polarizing filter, a green filter, a red filter, a Maddox rod, and a pinhole, which are for auxiliary use. Further, reference numeral 157 denotes an indicator for indicating a position of a corneal vertex of the eye to be examined with respect to the optometric window 150.

In the case of using such an optometer including the phoropter for mechanically displaying an examination result, the examiner reads the numeric values displayed on the respective display portions of the phoropter and the scales indicated by the indication marks thereof. In addition, the examiner enters the read values to the computer device 130, or writes down the values concerned on a recording sheet such as a medical chart, thus recording the examination result.

However, in this conventional recording method, the displayed numeric values and the indicated scales are visually read, and accordingly, a reading error, an entering error, and a recording error are sometimes made. If such an artificial error occurs, then a possibility to cause a misdiagnosis owing to erroneous recording contents may increase. In addition, there is a possibility that a necessity of another examination occurs to burden the examiner and the subject. Further, for the examiner who must examine many subjects a day, it is supposed to be heavily burdensome and merciless to be expected to eliminate such errors.

Next, the trial frame is described. Similarly to the phoropter, the trial frame is one for imparting a collecting refractive power to the eyes to be examined, and is used in place of the phoropter. The collecting refractive power is imparted by using trial lenses (examination lenses) with various powers in a switching manner.

FIGS. 16A and 16B show a structure of the trial frame. FIG. 16A shows a structure of a trial frame 200, and FIG. 16B shows a structure of a trial lens 202 attached into lens holding frames 201R and 201L of the trial frame 200.

The trial lens 202 includes an annular frame 202a, a lens 202b held by the annular frame 202a, a protrusion 202c protruded integrally with an outer circumferential surface of the annular frame 202a toward the outside in the radius direction, and a tab 202d provided on a tip of the protrusion 202c. The lens 202b has a predetermined refractive power (such as spherical power and cylindrical power), and on the tab 202d, the refractive power of the lens 202b concerned is written. In an optometry using the trial frame, a large number of trial lenses 202 having various refractive powers are used.

The trial frame 200 includes a structure for imparting a correcting spherical power and correcting cylindrical power individually to the right eye to be examined and the left eye to be examined. The trial frame 200 includes left and right annular plate portions 200L and 200R as holding frame attachment bases, a bridge 200B also serving as a nosepiece, which couples the annular plate portions 200L and 200R continuously and integrally with each other, attachment plate portions 203L and 203R provided integrally with outer edge portions of the annular plate portions 200L and 200R, and temples 204L and 204R attached to these attachment plate portions 203L and 203R.

The lens holding frames 201L and 201R are held so as to be rotatable in the circumferential direction in the annular plate portions 200L and 200R. Onto the annular plate portions 200L and 200R, operation knobs 205L and 205R for rotationally operating the lens holding frames 201L and 201R are attached below the attachment plate portions 203L and 203R. By rotating the operation knobs 205L and 205R in directions of arrows B1 and B2, respectively, the lens holding frames 201L and 201R rotate in directions of arrows C1 and C2, respectively.

Further, scales 206L and 206R are formed along the circumferential direction on front faces of the annular plate portions 200L and 200R. These scales 206L and 206R represent cylindrical axis degrees of the trial lenses for imparting the correcting cylindrical powers. When the trial lens 202 is one for correcting the cylindrical power, the direction of the tab 202d thereof, that is, a position of each of the scales 206L and 206R, which is indicated by the protrusion 202c, represents the cylindrical axis degree at that time.

Provided on front faces of the lens holding frames 201L and 201R are lens receiving portions 207L and 207R in which plural grooves for receiving the trial lenses 202 are formed, and plate springs 208L and 208R for pressing the trial lenses 202 against the lens receiving portions 207L and 207R and holding the trial lenses 202 therein.

Also in an optometer using the trial frame as described above, it is necessary for the examiner to visually read the numeric values and the scales, which are mechanically displayed on the trial frame and the trial lenses, to enter the numeric values and the scales to the computer device 130, and to write down the values and the scales in the recording sheet. Accordingly, as in the case of the phoropter, the reading error, the entering error, and the recording error are sometimes made.

SUMMARY OF THE INVENTION

The present invention has been made in consideration of circumstances as described above. It is an object of the present invention to provide an optometer capable of recording an examination result without making an error even in a case of using an apparatus with a structure to mechanically display the examination result.

In order to achieve the above object, according to a first aspect of the present invention, there is provided an optometer including: an examination result display mechanism for displaying an examination result for an eye to be examined; imaging means for taking an image including the examination result display mechanism; and image analysis means for analyzing the image taken by the imaging means to acquire the examination result displayed by the examination result display mechanism.

According to a second aspect of the invention, there is provided an optometer according to the first aspect of the present invention, in which: the examination result display mechanism displays the examination result by numeric values; and the image analysis means acquires the examination result by recognizing a pattern of a shape of the numeric value in the image taken by the imaging means.

According to a third aspect of the invention, there is provided an optometer according to the second aspect of the present invention, further including: target presentation means for presenting a target to the eye to be examined; and refractive power correcting means disposed to oppose the target presentation means and for imparting, to the eye to be examined to which the target is presented, at least one of spherical powers and cylindrical powers with various frequencies for correcting a refractive power of the eye to be examined, in which the examination result display mechanism is provided to the refractive power correcting means, and displays the at least one of a spherical power and a cylindrical power imparted to the eye to be examined by numeric values.

According to fourth to fifth aspects of the invention, there is provided an optometer according to the second or third aspect of the present invention, in which: the imaging means includes an imaging element for detecting imaging light and converting the imaging light into an electric signal; and the numeric values are formed of a color within a wavelength in which a photosensitivity of the imaging element is high.

According to a sixth aspect of the invention, there is provided an optometer according to the first aspect of the present invention, in which: the examination result display mechanism includes a scale representing a measurement range in an examination relating to the examination result, and an indication mark indicating a position on the scale, the position corresponding to the examination result; and the image analysis means detects the position of the indication mark in the image taken by the imaging means, and acquires the examination result based on the detected position of the indication mark.

According to a seventh aspect of the invention, there is provided an optometer according to the sixth aspect of the present invention, in which: the target presentation means for presenting a target to the eye to be examined; and refractive power correcting means disposed to oppose the target presentation means and for imparting, to the eye to be examined to which the target is presented, at least one of cylindrical powers and prism powers with various frequencies for correcting refractive power of the eye to be examined, wherein: the examination result display mechanism is provided to the refractive power correcting means; and the scale represents a measurement range of at least one of a cylindrical axis degree of a cylindrical power and a prism power imparted to the eye to be examined.

According to an eighth aspect of the invention, there is provided an optometer according to the sixth aspect of the present invention, in which: the scale represents a measurement range of an inter-pupil distance of the eye to be examined.

According to a ninth aspect of the invention, there is provided an optometer according to the third or sixth aspect of the present invention, in which: the imaging means includes an imaging element for detecting imaging light and converting the imaging light into an electric signal; and at least one of the scale and the indication mark is formed of a color within a wavelength in which a photosensitivity of the imaging element is high.

According to a tenth aspect of the invention, there is provided an optometer according to the seventh aspect of the present invention, in which: the imaging means includes an imaging element for detecting imaging light and converting the imaging light into an electric signal; and at least one of the scale and the indication mark is formed of a color within a wavelength in which a photosensitivity of the imaging element is high.

According to an eleventh aspect of the invention, there is provided an optometer according to the eighth aspect of the present invention, in which: the imaging means includes an imaging element for detecting imaging light and converting the imaging light into an electric signal; and at least one of the scale and the indication mark is formed of a color within a wavelength in which a photosensitivity of the imaging element is high.

According to a twelfth aspect of the invention, there is provided an optometer according to the third aspect of the present invention, in which: the refractive power correcting means is a phoropter incorporating plural correcting lenses therein, and for disposing the plural correcting lenses in a switching manner immediately in front of the eye to be examined; and the examination result display mechanism is provided to a front face of the phoropter.

According to a thirteenth aspect of the invention, there is provided an optometer according to the seventh aspect of the present invention, in which: the refractive power correcting means is a phoropter incorporating plural correcting lenses therein, and for disposing the plural correcting lenses in a switching manner immediately in front of the eye to be examined; and the examination result display mechanism is provided to a front face of the phoropter.

According to a fourteenth aspect of the invention, there is provided an optometer according to the third aspect of the present invention, in which: the refractive power correcting means includes plural trial lenses having correcting lenses and tabs displaying refractive powers of the correcting lenses, and a trial frame into which the plural trial lenses are selectively attachable; and the examination result display mechanism includes the tabs of the trial lenses.

According to a fifteenth aspect of the invention, there is provided an optometer according to the seventh aspect of the present invention in which: the refractive power correcting means includes plural trial lenses having correcting lenses and tabs displaying refractive powers of the correcting lenses, and a trial frame into which the plural trial lenses are selectively attachable; and the examination result display mechanism includes the tabs of the trial lenses.

The optometer in accordance with the present invention includes the imaging means for taking the image, which includes the examination result display mechanism for displaying the examination result, and the image analysis means for analyzing the image taken by the imaging means and acquiring the examination result displayed on the examination result display mechanism. Accordingly, it is not necessary to visually read the displayed examination result, to enter the examination result to the computer device, or to write down the examination result in the recording sheet. Hence, even in the case of using the apparatus structured to mechanically display the examination result, the examination result can be recorded without making an error.

BRIEF DESCRIPTION OF THE DRAWINGS

In the accompanying drawings:

FIGS. 16A and 16B are schematic views showing structures of a trial frame and a trial lens, which are applicable to the optometer, in which FIG. 16A is a front perspective view showing a schematic structure of the trial frame, and FIG. 16B is a front view showing a schematic structure of the trial lens.

DETAILED DESCRIPTION OF THE PREFERRED EMBODIMENTS

Figure 1:
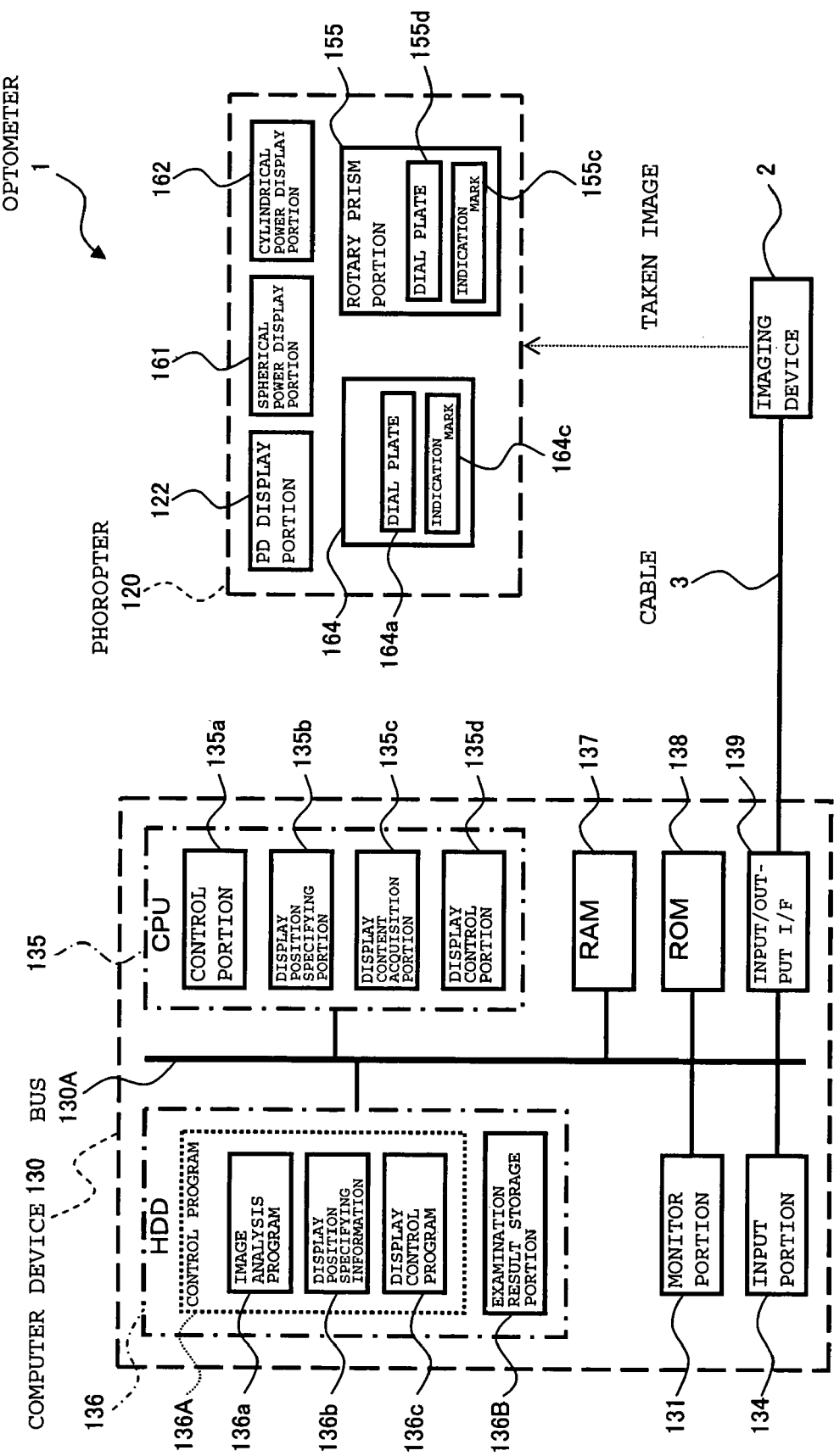
FIG. 1 is a block diagram showing an example of a schematic structure of an optometer according to an embodiment of the present invention.

A preferred embodiment of an optometer according to an embodiment of the present invention is described in detail with reference to the drawings.

The optometer of this embodiment has a substantially similar structure to the conventional optometer shown in FIGS. 11 to 16. Further, the optometer of this embodiment includes a phoropter or a trial frame as a subjective optometer. Constituents similar to those of the conventional optometer are described by using the reference numerals shown in FIGS. 11 to 16.

Further, as in the conventional optometer, an objective optometer (not shown) such as a refractometer is provided in the optometer of this embodiment. A measurement result by the objective optometer is automatically displayed on a monitor portion 131 of a computer device 130, and an examiner selects an initial value of a subjective optometry with reference to a value of the objective optometry.

[Apparatus Configuration]

FIG. 1 is a block diagram showing a structure of an example of the embodiment of the optometer according to the present invention. An optometer 1 shown in this drawing incorporates plural correcting lenses as "refractive power correcting means" of the present invention for imparting a correcting refractive power to the eyes to be examined, and uses a phoropter 120 for disposing the plural correcting lenses in a switching manner immediately in front of the eyes to be examined. The optometer 1 further includes the computer device 130 and an imaging device 2. The computer device 130 and the imaging device 2 are connected to each other through a cable 3 so as to be communicable with each other.

<Phoropter>

The phoropter 120 includes spherical power display portions 161 for displaying correcting spherical powers, cylindrical power display portions 162 for displaying correcting cylindrical powers, cylindrical axis display portions 164 for displaying cylindrical axes (correcting cylindrical axes) at the time of correction, and rotary prism portions 155 for displaying prism values at the time of correction, which are individually provided in a right measurement unit 120R and a left measurement unit 120L, as well as a PD display portion 122 for displaying a PD between the left and right eyes to be examined.

The PD display portion 122, the spherical power display portion 161, the cylindrical power display portion 162, the cylindrical axis display portion 164, and the rotary prism portion 155 hereinafter may also be sometimes referred to as a "display portion" collectively. Note that each of these components, a combination of a plurality thereof, or the entirety of the display unit is referred to as an "examination result display mechanism", in the present invention.

(PD Display Portion)

Figure 2:
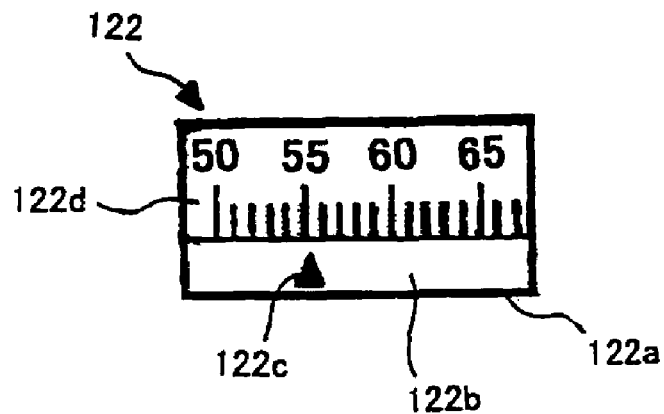
FIG. 2 is a schematic view showing an example of a structure of a PD display portion of a phoropter included in the optometer according to the embodiment of the present invention.

FIG. 2 shows an example of a display mode of the PD in the PD display portion 122. The PD display portion 122 is mechanically structured, which includes an opening portion 122a formed in a support unit 120A, a fixing plate 122b fixed to the opening portion 122a, an indication mark 122c formed on the fixing plate 122b, and a moving plate 122d provided so as to move crosswise in the opening portion 122a in response to approaching/separating actions of the measurement units 120R and 120L, which follow a rotation of PD change knobs 121.

Provided on the moving plate 122d is a scale, which represents a measurement range of a distance (PD) between optical axes of lenses disposed in the respective optometric windows 150 of the measurement units 120R and 120L. A position on the scale, which is indicated by the indication mark 122c, represents a value of the PD at the time concerned. The scale on the moving plate 122d is provided by, for example, a pitch of one millimeter in a range of 50 to 78 millimeters.

(Spherical Power Display Portion)

Figure 3:
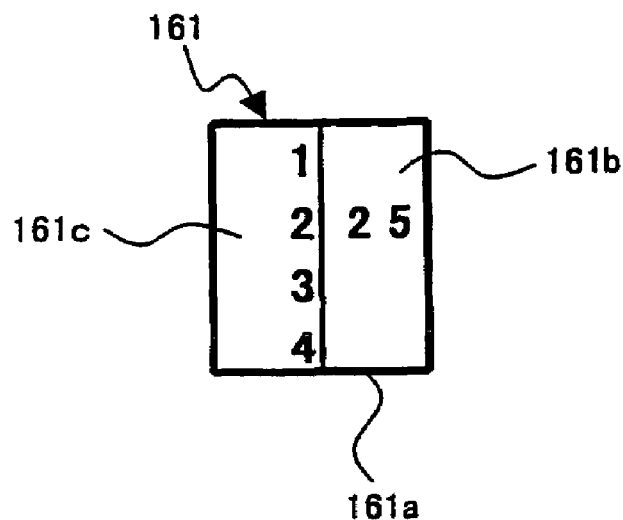
FIG. 3 is a schematic view showing an example of a structure of a spherical power display portion of the phoropter included in the optometer according to the embodiment of the present invention.

FIG. 3 shows an example of a display mode of the correcting spherical power in the spherical power display portion 161. The spherical power display portion 161 is mechanically structured, which includes an opening portion 161a formed in the right measurement unit 120R, and first and second moving plates 161b and 161c moving vertically in response to an operation of a spherical power changing portion 151. The first moving plate 161b displays portions of spherical power below a decimal point, and the second moving plate 161c displays integer portions of the spherical power.

Further, numeric values of "00", "25", "50", and "75" are written on the second moving plate 161c. Those numeric values are the fractional portion of the spherical power and mean that the displayed spherical power are 0.00, 0.25, 0.50, and 0.75 diopters, and so on. The values are disposed on the opening portion 161a in interlocking with a change of the spherical power by 0.25 diopters by a first change knob 151a.

Further, numeric values of "1", "2", "3", "4", and the like are written on the second moving plate 161c. Those numeric values mean that the displayed integer portions of the spherical power are 1, 2, 3, and 4 diopters, and so on. In this embodiment, four numeric values are displayed at once on the opening portion 161a. Note that larger numeric values and/or smaller numeric values than those numeric values are also written on the second moving plate 161c, and the values, including "1" to "4" and the larger and/or smaller ones than these are disposed on the opening portion 161a in interlocking with a change of the spherical power by 0.25 diopters by a first change knob 151a and a change thereof by 3 diopters by a second change knob.

Here, a spherical power display portion 161 of the left measurement unit 120L also includes the same structure as described above. The spherical power display portion 161 of the right measurement unit 120R and the spherical power display portion 161 of the left measurement unit 120L hereinafter may also be denoted by reference numerals "161R" and "161L", respectively.

(Cylindrical Power Display Portion)

Figure 4:
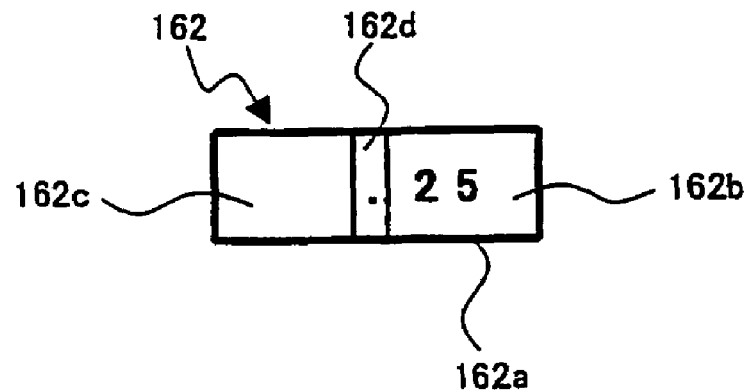
FIG. 4 is a schematic view showing an example of a structure of a cylindrical power display portion of the phoropter included in the optometer according to the embodiment of the present invention.

FIG. 4 shows an example of a display mode of the correcting cylindrical power in the cylindrical power display portion 162. The cylindrical power display portion 162 is mechanically structured, which includes an opening portion 162a formed in the right measurement unit 120R, first and second moving plates 162b and 162c moving vertically in response to a rotational operation of a cylindrical power changing portion 152, and a fixing plate 162d fixed between the first and second moving plates 162b and 162c. The first moving plate 162b displays the fractional portion of the cylindrical power, and the second moving plate 162c displays integer portion of the cylindrical power. Further, the decimal point is written on the fixing plate 162d.

Numeric values of "25", "50" and "75" are written on the first moving plate 162b. Those numeric values stand for cylindrical powers of 0.25, 0.50 and 0.75, and are sequentially disposed on the opening portion 162a in interlocking with a change of the cylindrical power by 0.25 diopters by the cylindrical power changing portion 152. Note that, when the fractional portion of the cylindrical power is 0, nothing is displayed on the first moving plate 162b.

Further, numeric values of "1", "2", "3", and the like are written on the second moving plate 162c. Those numeric values each stand for cylindrical powers of 1, 2, 3 diopters, and so on. Those numeric values are structured so as to be disposed one by one on the opening portion 162a. The second moving plate 162c is moved vertically so that the numeric value disposed on the opening portion 162a is incremented/decremented one by one every time when the cylindrical power changing portion 152 is rotated by four steps in the same direction (because a product of 0.25 diopters and 4 steps is equal to 1 diopter). Note that, when the integer portion of the cylindrical power is 0, nothing is displayed on the second moving plate 162c.

Here, a cylindrical power display portion 162 of the left measurement unit 120L also includes the same structure as described above. The cylindrical power display portion 162 of the right measurement unit 120R and the cylindrical power display portion 162 of the left measurement unit 120L hereinafter may also be denoted by reference numerals "161R" and "161L", respectively.

(Cylindrical Axis Display Portion)

Figure 14:
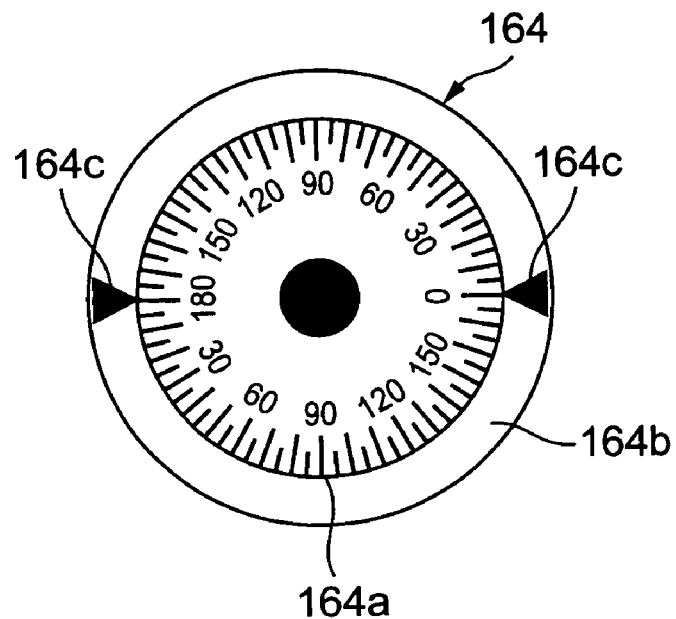
FIG. 14 is a schematic view showing an example of a cylindrical power display portion of the phoropter included in the optometer.

As described with reference to FIG. 14, the cylindrical axis display portion 164 is mechanically structured, which includes a disc-like dial plate 164a in which a scale representing a measurement range of a cylindrical axis degree is provided on a peripheral edge portion, and indication marks 164c provided on an edge end portion 164b on the periphery of the dial plate 164a and for indicating the scale on the dial plate 164a. On the scale on the dial plate 164a, the cylindrical axis degrees of 0° to 180° are written twice. The dial plate 164a is not rotated even if a lens support plate 153 and a cross cylinder lens portion 154 are rotated, and a line of 0 to 180° is always located horizontally. Further, the indication marks 164c are provided in a pair at positions opposite to each other with the dial plate 164a interposed therebetween, and individually indicate scales of the same frequency as that of the dial plate 164a. The edge end portion 164b on which the indication marks 164c are provided is structured so as not to rotate even if the lens support plate 153 is rotated.

The edge end portion 164b on which the indication marks 164c are provided is structured so as to rotate about a shaft 153a as a center by the same degree as a displacement of the cylindrical axis degree of the cylindrical lens 154a in interlocking with the rotation of the cross cylinder lens portion 154. In such a way, the indication marks 164c indicate the scales equal to the cylindrical axis degree of the cylindrical lens 154a. The cylindrical axis display portion 164 of the right measurement unit 120R and the cylindrical axis display portion 164 of the left measurement unit 120L hereinafter may also be denoted by reference numerals "164R" and "164L", respectively.

(Rotary Prism Portion)

Figure 15:
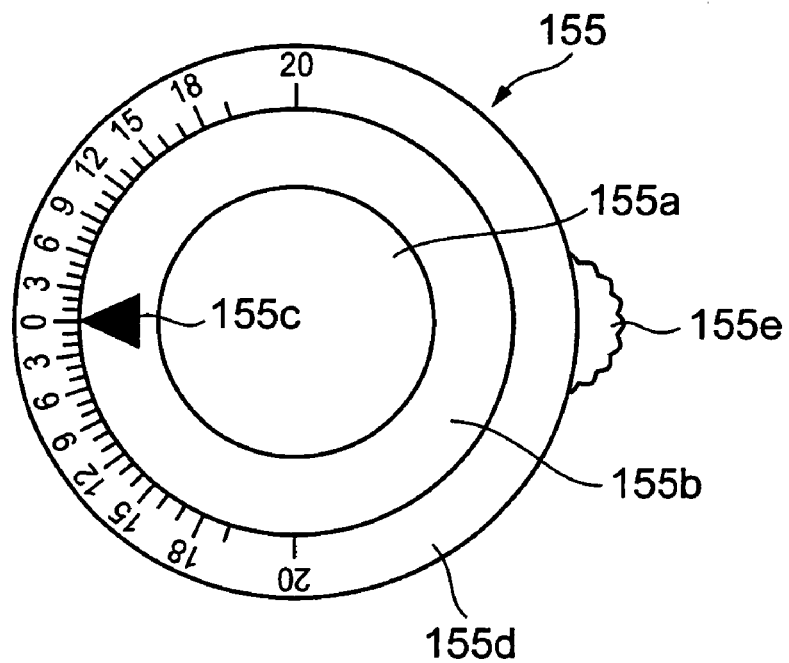
FIG. 15 is a schematic view showing an example of a structure of a rotary prism portion of the phoropter included in the optometer.

The rotary prism portion 155 is mechanically structured as described with reference to FIG. 15. The rotary prism portion 155 has a structure including a prism portion 155a including two lenses for generating prism power, a holding portion 155b for holding the two lenses of the prism portion 155a, an indication mark 155c provided on the holding portion 155b, an annular dial plate 155d on which a scale representing a measurement range of the prism power is provided, and a change dial 155e for changing the prism power by rotating the respective lenses of the prism portion 155a. The dial plate 155d is structured so as not to rotate even if the lens support plate 153 and the prism portion 155a are rotated, in which a line of "20" to "20" is always located vertically. Further, the holding portion 155b on which the indication mark 155c is provided is structured so as not to rotate even if the lens support plate 153 is rotated.

The two lenses of the prism portion 155a individually have prism power of 10 prism diopters. The lenses are rotated by operating the change dial 155e, thus making it possible for the prism portion 155a to generate prism power of 0 to 20 prism diopters. Further, those two lenses are rotated together, thus making it possible to change a prism base direction. On the dial plate 155d, a scale is provided within the range of 0 to 20 prism diopters in accordance with the prism base direction (of raising and lowering the base).

When the change dial 155e is rotated, the holding portion 155b is rotated together with the lenses of the prism portion 155a, and the indication mark 155c on the holding portion 155b indicates the scale of the prism power generated by the prism portion 155a. The rotary prism portion 155 of the right measurement unit 120R and the rotary prism portion 155 of the left measurement unit 120L hereinafter may also be denoted by reference numerals "155R" and "155L", respectively.

<Imaging Device>

The imaging device 2 forms "imaging means" of the present invention, and is used for taking an image (including the display portion) of a front face of the phoropter 120. For this purpose, the imaging device 2 is disposed, for example, on a cabinet of the optotype device 140 shown in FIG. 11 or in the inside thereof, so as to oppose the front face of the phoropter 120. Note that the optotype device 140 forms "target presentation means" of the present invention.

Figure 5:
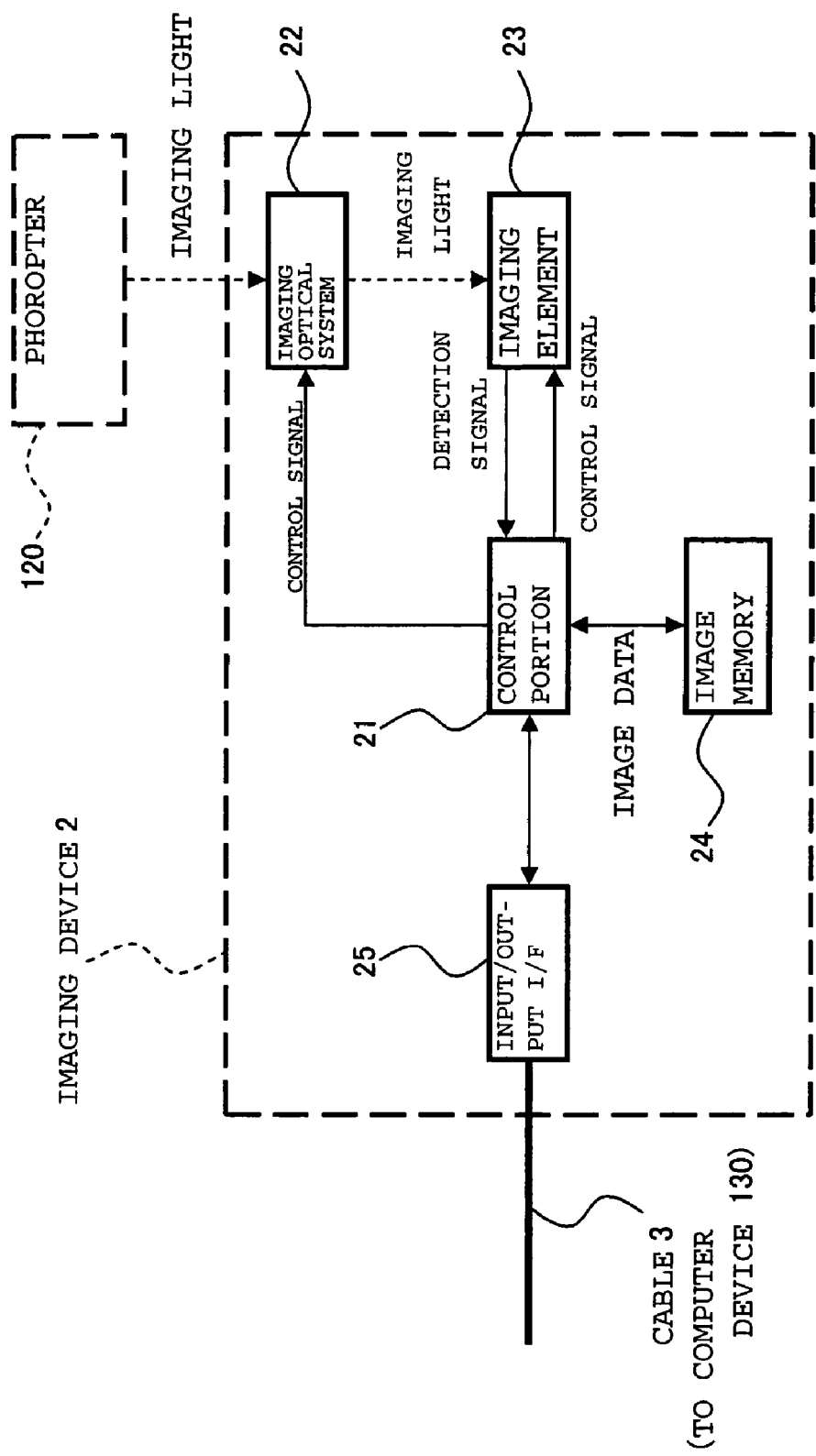
FIG. 5 is a block diagram showing a schematic structure of an example of an imaging device included in the optometer according to the embodiment of the present invention.

FIG. 5 shows a schematic structure of the imaging device 2. The imaging device 2 has a structure including a control portion 21, an imaging optical system 22, an imaging element 23, an image memory 24 and an input/output I/F 25.

The control portion 21 includes a storage device such as a ROM storing a program for controlling the respective units of the imaging device 2, and an arithmetic and control portion such as a CPU for executing the program. In particular, the control portion 21 exercises control over a change of an imaging magnification and a focusing in the imaging optical system 22, a timing of the imaging element 23, storing image data in the image memory 24, reading the image data therefrom, transmitting/receiving the data by the input/output I/F 25, and the like.

In the imaging optical system, although not shown, optical elements such as an objective lens, a variable power lens, and an imaging lens are provided, together with a drive device such as a solenoid and a stepping motor for driving those optical elements. The imaging optical system 22 functions to form an image on an imaging surface of the imaging element 23 upon receiving light (imaging light) from the front surface of the phoropter 120.

The imaging element 23 is formed of a CCD (Charge Coupled Devices), a CMOS (Complementary Metal Oxide Semiconductor), or the like, and operates so as to detect the imaging light guided from the imaging optical system 22, to convert the imaging light into an electric signal (detection signal), and to output the electric signal. Note that it is desirable that the imaging element 23 with a large number of pixels be used so as to obtain a high-quality image, thereby achieving higher image quality and a higher sensitivity.

The detection signal from the imaging element 23 is stored as data (image data) of a taken image of the front face of the phoropter 120 in the image memory 24 by the control portion 21. The control portion 21 reads the image data from the image memory 24 at predetermined timing, and transmits the image data to the computer device 130 through the input/output I/F 25. Note that the detection signal by the imaging element 23 may be directly transmitted as the image data to the computer device 130. Here, the image memory 24 has a structure including an image memory and the like, and the input/output I/F 25 has a structure including a communication interface circuit and the like.

<Computer Device>

The computer device 130 has a structure including the monitor portion 131 formed of a liquid crystal display or the like, an input portion 134 formed of input devices such as a keyboard 132 and a mouse 133 (refer to FIG. 11), a CPU (Central Processing Unit) 135 for performing a variety of arithmetic processing and control processing based on computer programs and data, a hard disk drive (HDD) 136 for storing the various computer programs and data, a RAM (Random Access Memory) 137 in which the programs and the data which are executed by the CPU 135 are developed, a ROM (Read Only Memory) 138 in which basic programs and data are stored, and an input/output interface (I/F) 139 for performing input/output of information from/to an external device such as the imaging device 2. Those respective portions are mutually connected by a bus 130A.

(HDD)

First, the HDD 136 is described. A control program 136A for executing processing to be described later according to the present invention is stored in advance in the HDD 136. The control program 136A is installed from a recording medium such as a CD-ROM and a DVD-ROM or from a server or the like via a network such as a LAN.

The control program 136A includes an image analysis program (routine) 136*a* for analyzing an image taken by the imaging device 2, display position specifying information 136*b* referred to in the analysis processing for the taken image, and a display control program (routine) 136*c* for performing display processing in the monitor portion 131. The image analysis program 136*a* and the display control program 136*c* are described in detail in a description of the CPU 135 for executing those programs.

Figure 6:
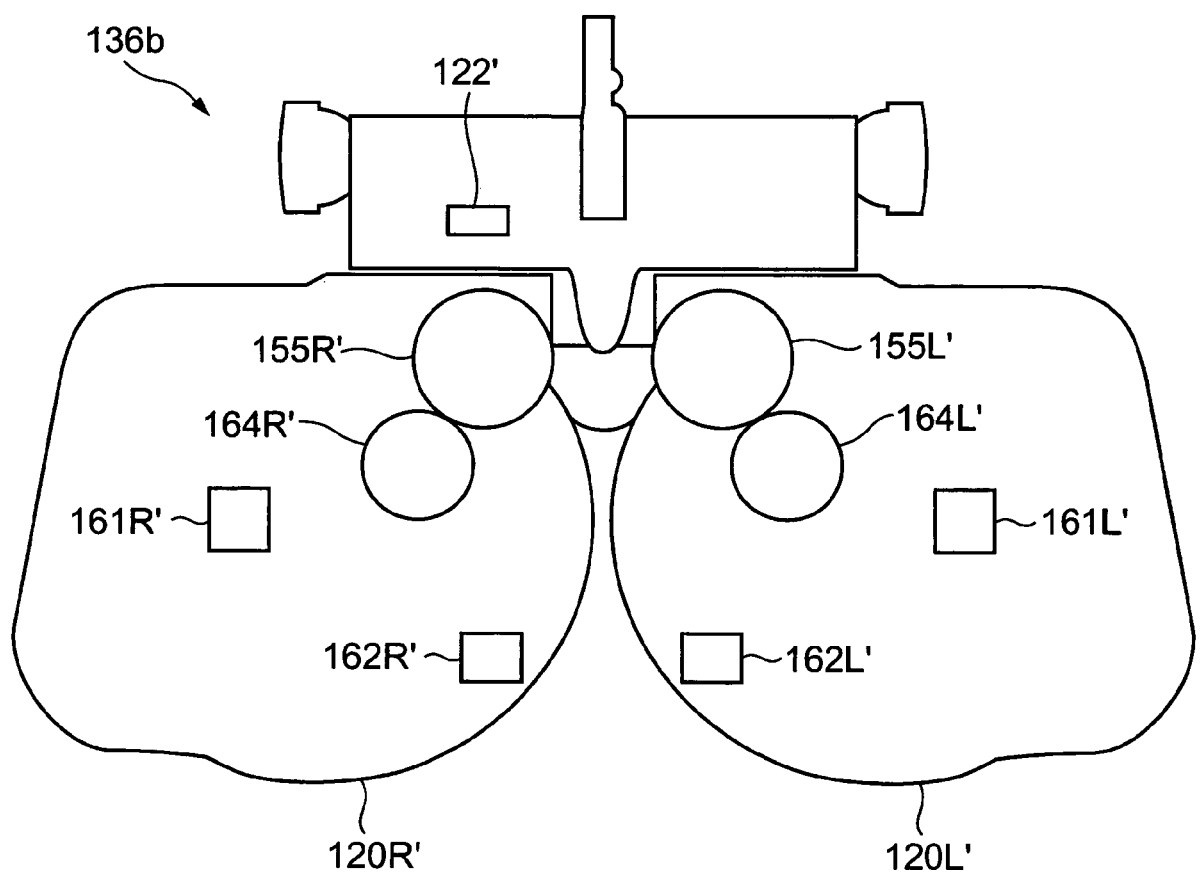
FIG. 6 is a view showing an example of display position specifying information stored in a computer device included in the optometer according to the embodiment of the present invention.

The display position specifying information 136*b* has a structure including positional information of the respective display portions on the front face of the phoropter 120. FIG. 6 shows an example of the display position specifying information 136*b*.

The display position specifying information 136*b* shown in FIG. 6 is image information creating a pattern image of the front face of the phoropter 120. The display position specifying information 136*b* includes a spherical power display portion pattern 161R' representing a position of the spherical power display portion 161R, a cylindrical power display portion pattern 162R' representing a position of the cylindrical power display portion 162R, a cylindrical axis display portion pattern 164R' representing a position of the cylindrical axis display portion 164R, and a rotary prism portion pattern 155R' representing a position of the rotary prism portion 155R, as well as an outer edge pattern 120R' of the right measurement unit 120R. In a similar way, the display position specifying information 136*b* includes a spherical power display portion pattern 161L' representing a position of the spherical power display portion 161L, a cylindrical power display portion pattern 162L' representing a position of the cylindrical power display portion 162L, a cylindrical axis display portion pattern 164L' representing a position of the cylindrical axis display portion 164L, and a rotary prism portion pattern 155L' representing a position of the rotary prism portion 155L, as well as an outer edge pattern 120L' of the left measurement unit 120L. Further, the display position specifying information 136*b* includes a PD display portion pattern 122' representing a position of the PD display portion 122.

The display position specifying information 136*b* as described above is created by, for example, extracting the positions of the respective display portions from the taken image of the front face of the phoropter 120.

Note that the display position specifying information 136*b* for use in the present invention is not limited to the image information as described above. Information of any mode is usable as long as the information makes it possible to specify the positions of the respective display portions from the image (that is, image data) of the front face of the phoropter 120, which is taken by the imaging device 2. As an example of this, the display position specifying information 136*b* can be composed of coordinate values of the respective display portions in the taken image of the front face of the phoropter 120. Note that two-dimensional coordinates defined arbitrarily on the imaging surface of the imaging element 23 and two-dimensional coordinates defined arbitrarily on the taken image are usable as coordinates serving as references of the coordinate values concerned.

In the HDD 136, there is formed a directory for storing examination results (spherical power, cylindrical power, cylindrical axis degree, prism value, PD and the like) displayed on the display portions on the front face of the phoropter 120. This directory is referred to as an examination result storage portion 136B.

(CPU)

The CPU 135 includes a display position specifying portion 135*b*, a display content acquisition portion 135*c* and a display control portion 135*d*, which are for executing the processing according to the present invention, as well as a control portion 135*a* for controlling the respective portions of the optometer 1.

The display position specifying portion 135*b* and the display content acquisition portion 135*c* form "image analysis means" of the present invention, and are composed of the CPU 135 for executing the image analysis program 136*a* of the control program 136A. The CPU 135 refers to the display position specifying information 136*b* when operating as the display position specifying portion 135*b*. Further, the display control portion 135*d* is composed of the CPU 135 for executing the display control program 136*c*. Description will be made of processing performed by the display position specifying portion 135*b*, the display content acquisition portion 135*c*, and the display control portion 135*d*.

(Display Position Specifying Portion)

The display position specifying portion 135*b* performs processing for analyzing the image on the front face of the phoropter 120, which is taken by the imaging device 2, and specifying the positions of the respective display portions on the image concerned. An example of the processing is described in further detail.

First, the display position specifying portion 135*b* analyzes the image data transmitted from the imaging device 2, and detects outer edges of the respective measurement units 120R and 120L on the taken image. This detection processing is performed by, for example, comparing a color (respective densities of RGB, and the like) of the front face of the phoropter 120 with a color of a background image.

Next, the display position specifying portion 135*b* superposes the taken image onto the pattern image of the display position specifying information 136*b*. At this time, the outer edges thus detected of the respective measurement units 120R and 120L are superposed on the outer edge patterns 120R' and 120L' in the display position specifying information 136*b*, respectively. When a size of the outer edges on the taken image and a size of the outer edge patterns 120R' and 120L' differ from each other, either one or both of the taken image and the pattern image are adjusted in size, thus making both sizes thereof to coincide with each other.

Subsequently, the display position specifying portion 135*b* specifies the respective regions in the taken image, which are superposed on the respective display portion patterns in the pattern image of FIG. 6, as positions of the respective display portions of the phoropter 120. Specifically, the display position specifying portion 135*b* specifies: the region in the taken image superposed on the PD display-portion pattern 122' as the position of the PD display portion 122; the regions in the taken image individually superposed on the spherical power display portion patterns 161R' and 161L' as the positions of the spherical power display portions 161R and 161L; the regions in the taken image individually superposed on the cylindrical power display portion patterns 162R' and 162L' as the positions of the cylindrical power display portions 162R and 162L; the regions in the taken image individually superposed on the cylindrical axis display portion patterns 164R' and 164L' as the positions of the cylindrical axis display portions 164R and 164L; and the regions in the taken image individually superposed on the rotary prism portion patterns 155R' and 155L' as the positions of the rotary prism portions 155R and 155L. This is an example of the processing performed by the display position specifying portion 135*b*.

Note that the processing executed by the display position specifying portion 135*b* is not limited to such a mode as described above. For example, though the outer edges of the respective measurement units 120R and 120L are used to perform the superposition and size alignment of the taken image and the pattern image in the above-described processing, the superposition and the size alignment may also be performed by providing at least two marks on the front face of the phoropter 120. For this purpose, two (or more) image aligning marks are provided on the front face of the phoropter 120, and image aligning marks are further provided at corresponding positions in the pattern image of the display position specifying information 136*b*. Subsequently, by adjusting the image so that the marks on the front face and in the pattern image coincide with each other, both of the sizes and positions of the taken image and the pattern image can be made to coincide with each other.

(Display Content Acquisition Portion)

The display content acquisition portion 135*c* performs processing for analyzing each of the regions of the PD display portion 122, the spherical power display portions 161R and 161L, the cylindrical power display portions 162R and 162L, the cylindrical axis display portions 164R and 164L, and the rotary prism portions 155R and 155L, positions of which in the taken image are specified by the display position specifying portion 135*b*, and obtaining display contents in the respective portions.

With regard to the spherical power display portions 161R and 161L and the cylindrical power display portions 162R and 162L in the taken image, the display content acquisition portion 135*c* recognizes, for example, patterns of shapes of the respective numerical figures structuring the numeric values (refer to FIG. 3 and FIG. 4) displayed on the respective display portions, thereby acquiring the spherical powers and the cylindrical powers.

In the case of acquiring the spherical powers and the cylindrical powers by such a technique, the existing program for recognizing patterns of (at least) numerical figures 0 to 9 is provided in the image analysis program 136*a*. The display content acquisition portion 135*c* executes the program concerned, thereby performing the acquisition processing of the spherical powers and the cylindrical powers. Note that shape data (reference shape data) of the numerical figures, which serves as a reference in the pattern recognition of the numerical figures, is created based on, for example, numbers actually formed on the display portions of the phoropter.

Further, with regard to each of the cylindrical axis display portions 164R and 164L (refer to FIG. 14), the display content acquisition portion 135*c* obtains the position of the indication mark 164*c* in the taken image, and acquires the cylindrical axis degree based on the obtained position of the indication mark 164*c*. Here, as described above, the dial plate 164*a* is not rotated even if the cross cylinder lens portion 154 is rotated. Meanwhile, the indication mark 164*c* is structured to rotate together with the rotation of the cross cylinder lens portion 154. Note that the position of the indication mark 164*c* is detected as, for example, a displacement (degree, distance, and the like) from a predetermined reference position (for example, position indicating 0° and 180°).

The reading processing of the cylindrical axis degrees displayed on the cylindrical axis display portions 164R and 164L can be realized by, for example, detecting the positions of the indication marks 164*c* in the taken image, and obtaining the scale indicated by the indication marks 164*c*, based on a result of the detection. As an example of this, as shown in FIG. 14, if it is detected that the displacement of the indication marks 164*c* in the taken image from the above-described reference position is 0°, the cylindrical axis degree is determined to be 0°. If it is detected that the displacement from the above-described reference position is 90°, the cylindrical axis degree is determined to be 90°. Further, if it is detected that the displacement of the left indication mark 164*c* from the above-mentioned reference position is 45° in the upward direction, and if it is detected that the displacement of the right indication mark 164*c* from the above-described reference position is 45° in the downward direction, the cylindrical axis degree is determined to be 135°.

In the image analysis program 136*a*, information indicating such a correspondence between the positions of the indication marks 164*c* and the scales on the dial plate 164*a* is provided in advance. The display content acquisition portion 135*c* obtains the cylindrical axis degree with reference to the information. Note that, since the numeric values indicated by the left and right indication marks 164*c* are the same, the display content acquisition portion 135*c* may also be structured to obtain the position of only one of the indication marks 164*c*.

Further, also with regard to each of the rotary prism portions 155R and 155L (refer to FIG. 15), the display content acquisition portion 135*c* obtains the position of the indication mark 155*c* in the taken image, and acquires the prism power based on the obtained position of the indication mark 155*c*. Here, as described above, the dial plate 155*d* is not rotated even if the change dial 155*e* is operated to rotate the prism portion 155*a*, in which the line of "20" to "20" is always located vertically. Meanwhile, the indication mark 155*c* is structured to rotate together with the rotation of the prism portion 155*a*. Note that the position of the indication mark 155c is detected as, for example, a displacement (degree, distance, and the like) from a predetermined reference position (for example, position indicating "0").

The reading processing of the prism power displayed on the rotary prism portions 155R and 155L can be realized by, for example, detecting the positions of the indication marks 155c in the taken image, and obtaining the scale indicated by the indication marks 155c, based on a result of the detection. As an example of this, as shown in FIG. 15, if it is detected that the displacement of the indication marks 155c in the taken image from the above-described reference position is 0°, the prism power is determined to be 0. If it is detected that the displacement from the above-described reference positions is 90° in the upward direction, the prism power is determined to be 20.

Note that, when the indication mark 155c is located upward from the above-described reference position, it is indicated that the prism base is raised, and when the indication mark 155c is located downward therefrom, it is indicated that the prism base is lowered. Here, as seen from FIG. 15, when the position of the indication mark 155c is specified, the prism power indicated by the indication mark 155c (including distinction between the raise and lowering of the base) is uniquely determined.

In the image analysis program 136a, information indicating such a correspondence between the positions of the indication marks 155c and the scales on the dial plate 155d is provided in advance. The display content acquisition portion 135c obtains the prism power with reference to the information.

In the PD display portion 122 shown in FIG. 2, the position of the indication mark 122c is fixed, and the moving plate 122d having the scale with the range of 50 to 78 millimeters moves. On the moving plate 122d, numeric values "50", "55", "60", "65", "70", and "75" are indicated. For example, the display content acquisition portion 135c recognizes patterns of shapes of the numerical figures structuring those numeric values, thereby detecting positions thereof, and detects the position of the indication mark 122c. Subsequently, the display content acquisition portion 135c obtains a relative position of the numeric values obtained by such a pattern recognition and the indication mark 122c, thereby acquiring a value indicated by the indication mark 122c as the PD. As an example, when the positions of the numeric values "55" and "60" and the position of the indication mark 122c are detected, and the indication mark 122c is located at a position where a distance between the numeric values "55" and "60" is interiorly divided in a ratio of 2:3, the value indicated by the indication mark 122c is "57", and "57" is acquired as the PD.

The control portion 135a stores the display contents of the respective display portions, which are acquired by the display content acquisition portion 135, as electronic data in the examination result storage portion 136B of the HDD 136 in association with the display positions specified by the display position specifying portion 135b.

Specifically, the control portion 135a stores: the display content of the PD display portion 122 as a value of the PD between the left and right eyes to be examined; the display content of the spherical power display portion 161R as the correcting spherical power of the right eye to be examined; the display content of the spherical power display portion 161L as the correcting spherical power of the left eye to be examined; the display content of the cylindrical power display portion 162R as the correcting cylindrical power of the right eye to be examined; the display content of the cylindrical power display portion 162L as the correcting cylindrical power of the left eye to be examined; the display content of the cylindrical axis display portion 164R as the correcting cylindrical axis degree of the right eye to be examined; the display content of the cylindrical axis degree display portion 164L as the correcting cylindrical axis degree of the left eye to be examined; the display content of the rotary prism portion 155R as the correcting prism power of the right eye to be examined; and the display content of the rotary prism portion 155L as the correcting prism power of the left eye to be examined.

Note that in the case where the optometer 1 is connected to an electronic medical chart system, a structure can be made so that the display contents concerned (measurement value such as refractive powers of the eyes to be examined) can be automatically written into an electronic medical chart.

It is described that it is desirable that the taken image be high-quality in the above explanation of the imaging device 2, which makes it possible to accurately read the display contents of the respective display portions in the processing by the display content acquisition portion 135c.

(Display Control Portion)

The display control portion 135d performs processing for displaying the display contents of the respective display portions of the phoropter 120, which are acquired by the display content acquisition portion 135c, on the monitor portion 131 of the computer device 130.

Figure 7:
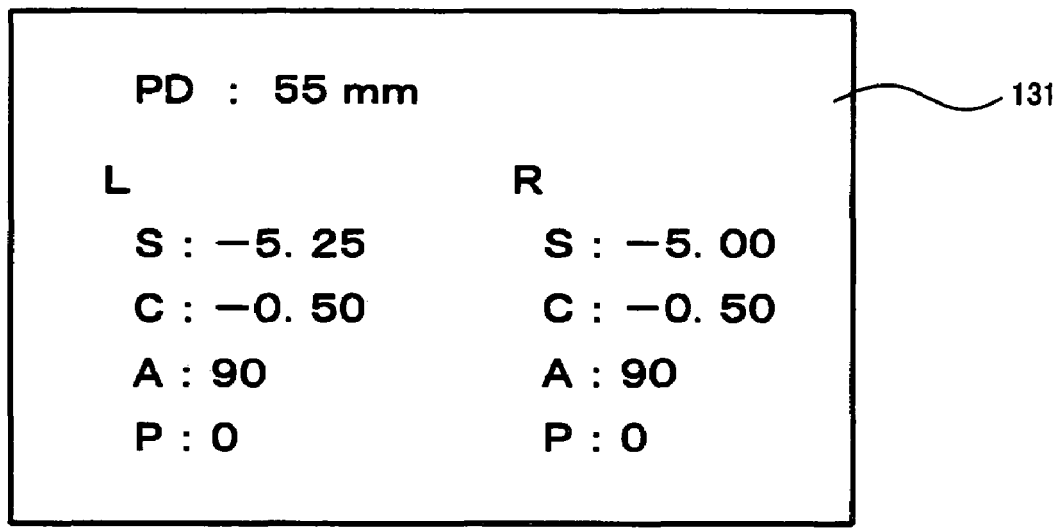
FIG. 7 is a table showing an example of a display mode of an examination result by the optometer according to the embodiment of the present invention.

The display control portion 135d displays the PD, the spherical powers, cylindrical powers, cylindrical axis degrees, prism values of the left and right eyes to be examined, and the like, which are acquired by the display content acquisition portion 135c and stored in the examination result storage portion 136B, on the monitor portion 131 in a format, for example, as shown in FIG. 7. FIG. 7 shows an example of a display mode of the examination results when the displayed PD is 55 (millimeters), with regard to the displayed values for the left eye to be examined, the spherical power S is −5.25 (diopters), the cylindrical power C is −0.50 (diopters), the cylindrical axis degree A is 90 (degree), and the prism power P is 0 (diopter), and with regard to the displayed values for the right eye to be examined, the spherical power S is −5.00, the cylindrical power C is −0.50, the cylindrical axis degree A is 90, and the prism power P is o. Note that, when the prism power P is not 0, the distinction between the raise and lowering of the base is also displayed. The display mode of the examination results by the display control portion 135d is not limited to such a display format as described above, and it is possible to employ an arbitrary display format.

[Processing Procedure]

Figure 8:
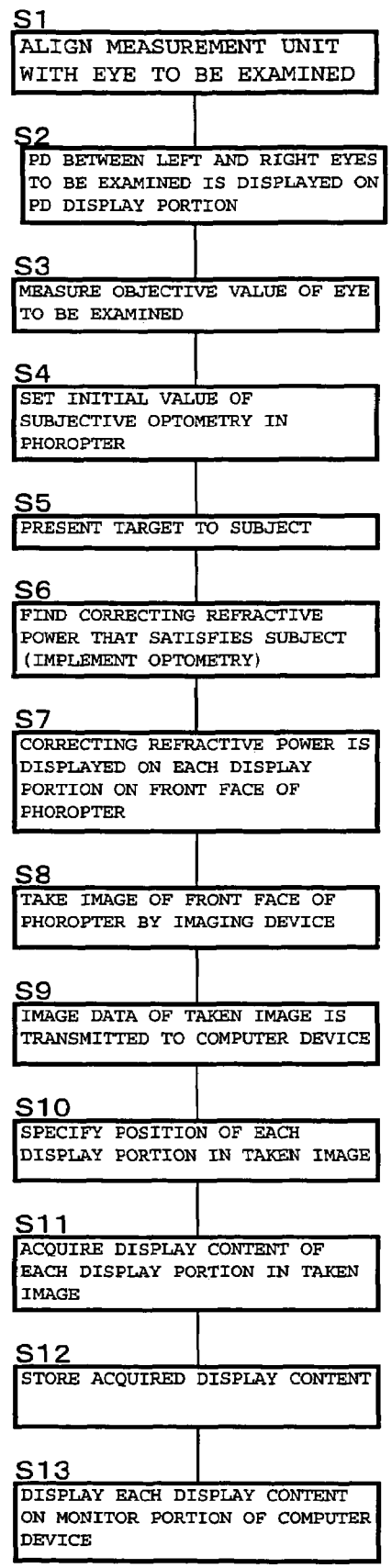
FIG. 8 is a flowchart showing an example of a processing procedure executed by the optometer according to the embodiment of the present invention.

Description is made of an example of a processing procedure by the optometer 1 structured as described above. FIG. 8 shows an example of a procedure of the optometry using the optometer 1.

Figure 9:
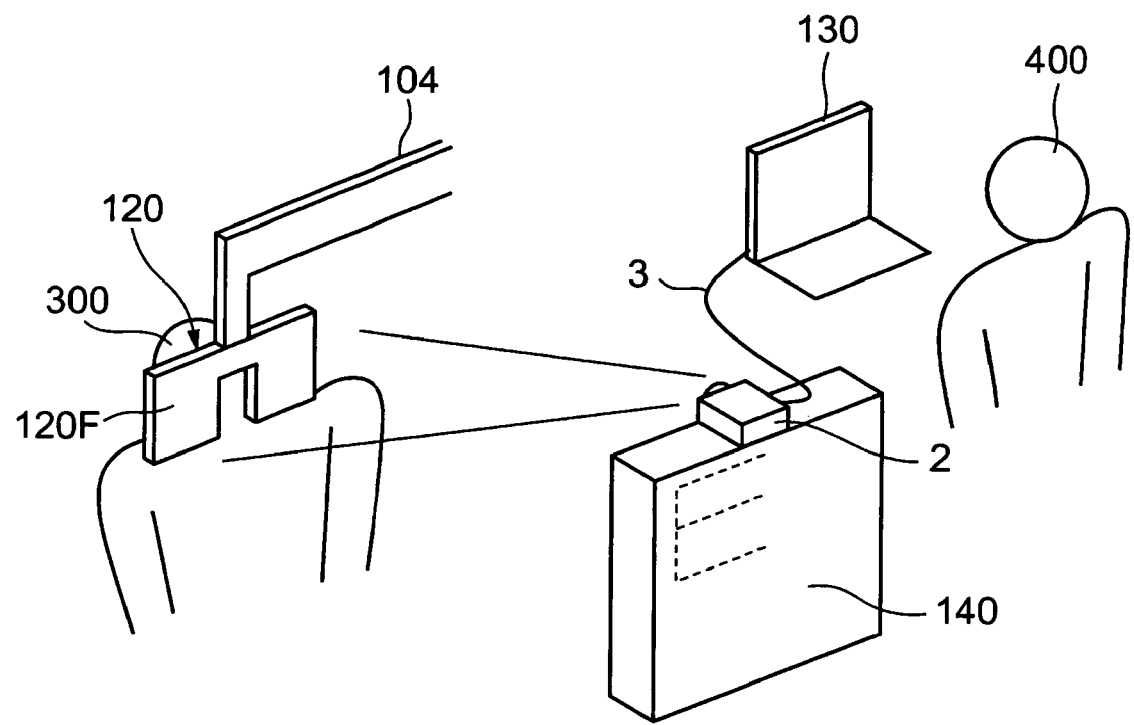
FIG. 9 is a schematic perspective view showing an optometry mode using the optometer according to the embodiment of the present invention.

FIG. 9 shows a mode of the optometry using the optometer 1. Reference numeral 120F in FIG. 9 denotes the front face of the phoropter 120. As described above, provided on the front face 120F of the phoropter 120 are the PD display portion 122, the spherical power display portions 161R and 161L, the cylindrical power display portions 162R and 162L, the cylindrical axis display portions 164R and 164L, and the rotary prism portions 155R and 155L. Further, reference numeral 300 denotes the subject, and reference numeral 400 denotes the examiner. Further, though the imaging device 2 in this drawing is disposed on the optotype device 140, the imaging device 2 may be disposed in the inside of the optotype device 140, and the like.

Figure 11:
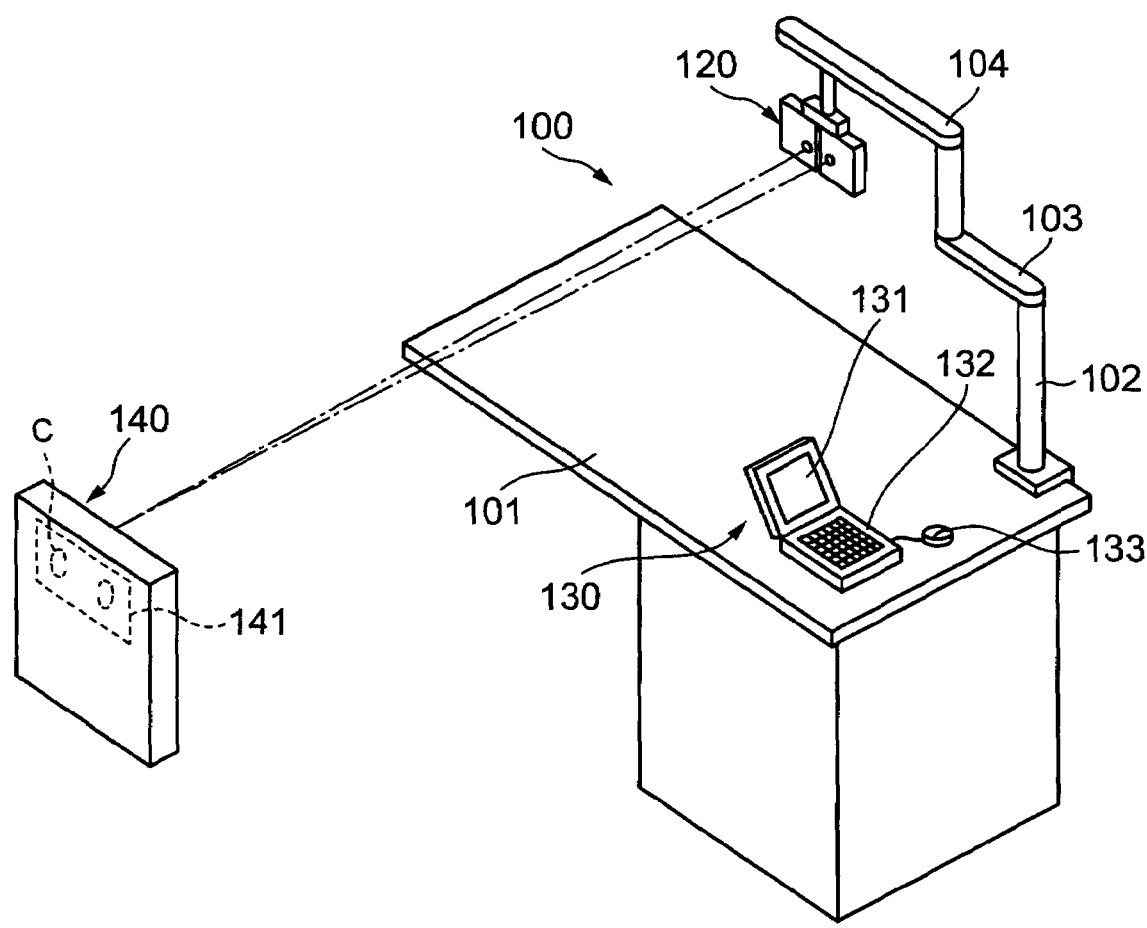
FIG. 11 is a perspective view showing an outline of an entire structure of an optometer.
Figure 12:
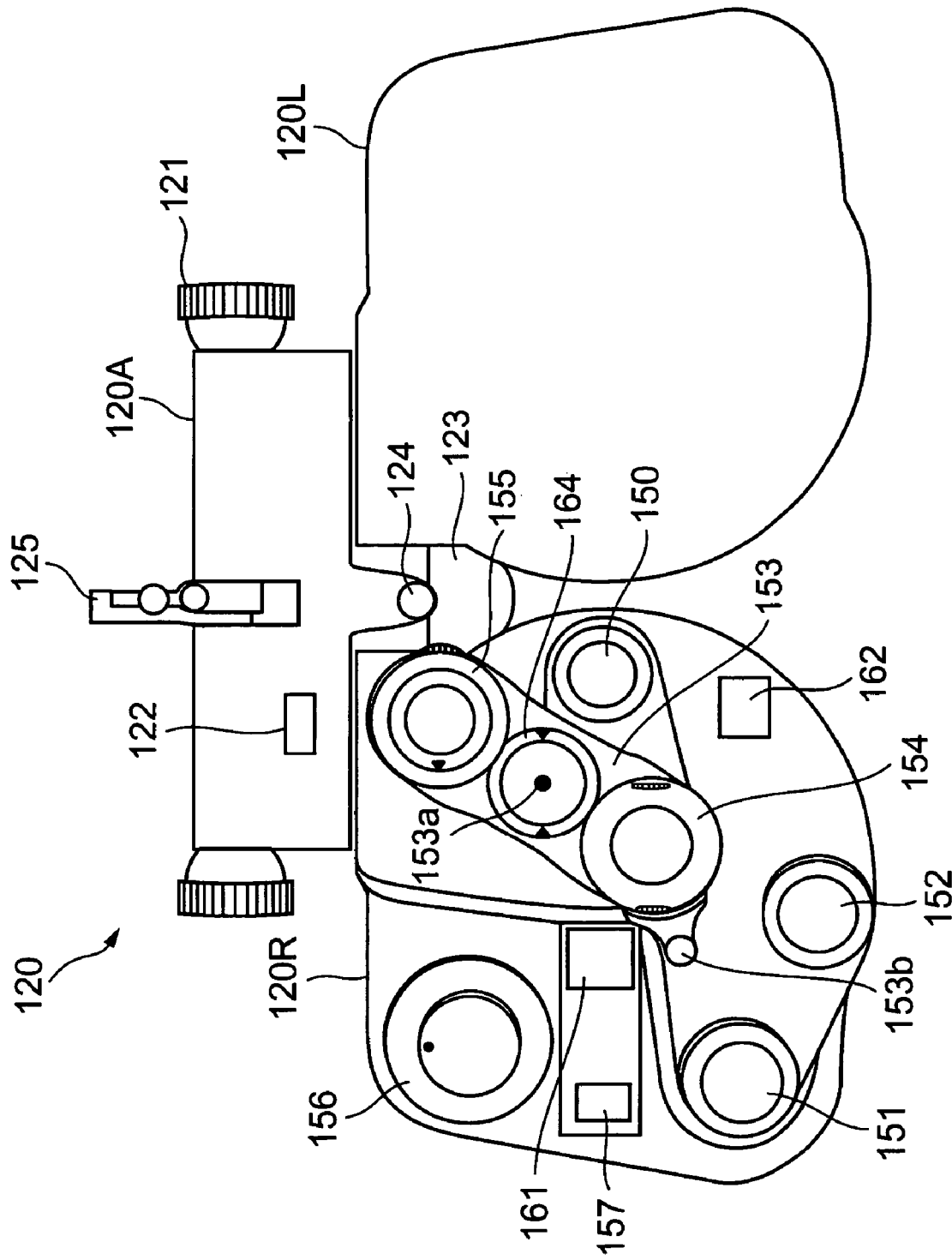
FIG. 12 is a schematic view showing a structure of a front face of a phoropter included in the optometer.
Figure 13:
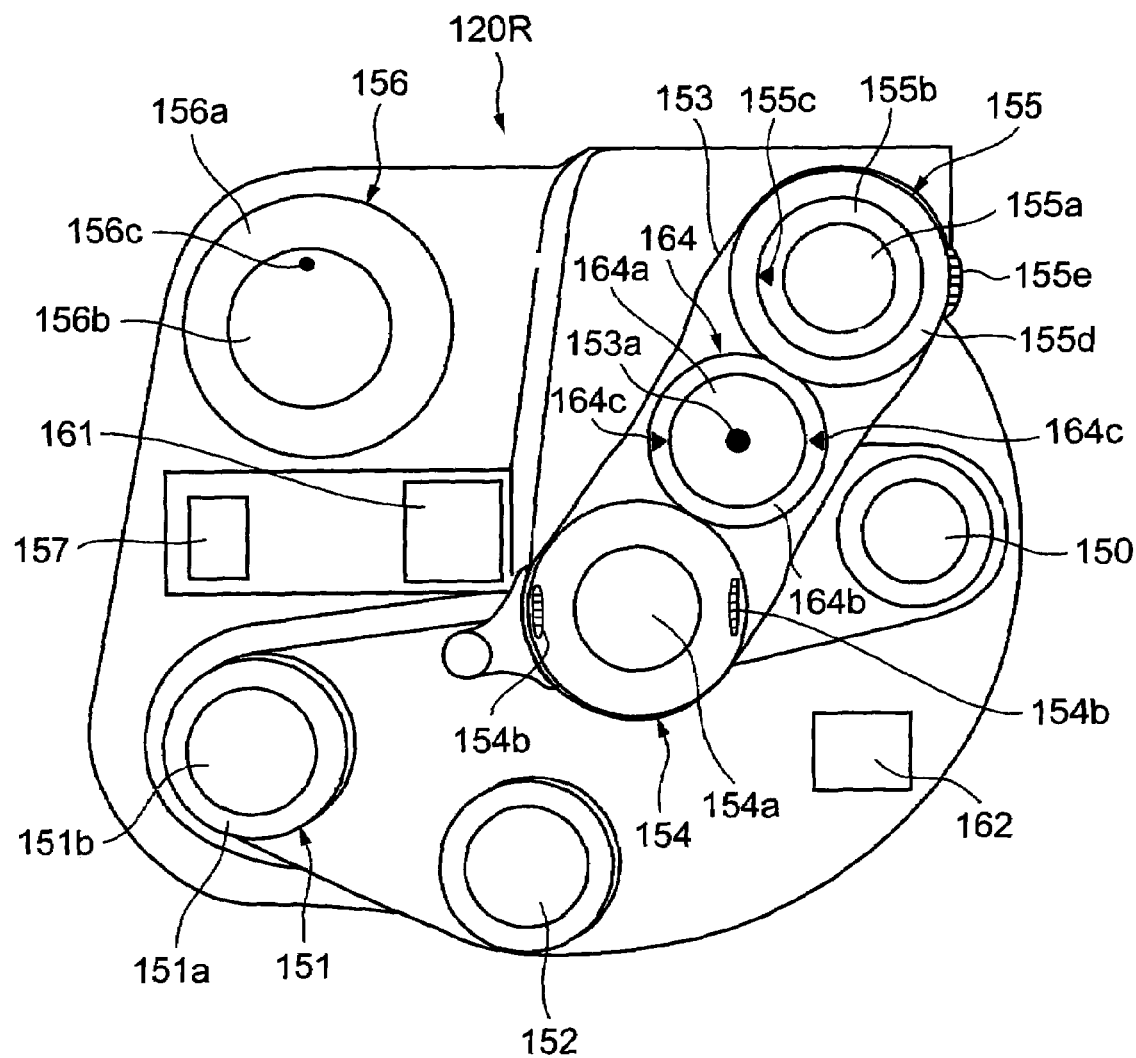
FIG. 13 is a schematic view showing a structure of a front face of a right measurement unit of the phoropter included in the optometer.

First, the examiner 400 seats the subject 300 in an optometric chair (not shown) beside the optometric table 101 shown in FIG. 11, and disposes the phoropter 120 in front of the face of the subject 300. In addition, the examiner 400 rotationally operates the PD change knobs 121 shown in FIG. 12, and makes an alignment so as to arrange the optometric windows 150 of the respective measurement units 120R and 120L immediately in front of the right eye to be examined and the left eye to be examined, respectively (S1). On the PD display portion 122, the value of the PD between the left and right eyes to be examined at this time is displayed as shown in FIG. 2 (S2).

Next, the values of the objective optometry for the left and right eyes to be examined of the subject 300 are measured by the objective optometer (not shown) such as the refractometer (S3). The obtained values of the objective optometry are displayed on the monitor portion 131 of the computer device 130. The examiner 400 sets the initial value of the subjective optometry in the phoropter 120 with reference to the values of the objective optometry (S4), and operates the optotype device 140 to allow the optotype device 140 to present the target C to the subject 300 (S5).

While changing the target C presented to the subject 300, the examiner 400 changes the correcting spherical power, the correcting cylindrical power, and the like by the phoropter 120, and consult with the subject 300 to examine how he/she sees the target C, thereby finding correcting refractive power that satisfies the subject 300. Then, the examiner 400 finishes the examination (S6).

At this time, on the front face 120F of the phoropter 120, the PD is displayed on the PD display portion 122, the spherical powers are displayed individually on the spherical power display portions 161R and 161L, the cylindrical powers are displayed individually on the cylindrical power display portions 162R and 162L, the cylindrical axis degrees are displayed individually on the cylindrical axis display portions 164R and 164L, and the prism values are displayed individually on the rotary prism portions 155R and 155L (S7). The examiner 400, for example, operates the input portion 134 of the computer device 130, thereby imaging the front face 120F of the phoropter 120 by the imaging device 2 (S8). The imaging device 2 transmits the image data of the image of the front face 120F of the phoropter 120 to the computer device 130 through the cable 3 (S9).

The display position specifying portion 135b of the CPU 135 of the computer device 130 analyzes the image taken by the imaging device 2, and specifies the respective positions of the PD display portion 122, the spherical power display portions 161R and 161L, the cylindrical power display portions 162R and 162L, the cylindrical axis display portions 164R and 164L, and the rotary prism portions 155R and 155L in the image (S10).

Next, the display content acquisition portion 135c of the CPU 135 individually analyzes the regions of the PD display portion 122, the spherical power display portions 161R and 161L, the cylindrical power display portions 162R and 162L, the cylindrical axis display portions 164R and 164L, and the rotary prism portions 155R and 155L, positions of which are specified by the display position specifying portion 135b, and acquires the display contents of the respective display portions (S11). The control portion 135a stores the acquired display contents as the electronic data in the examination result storage portion 136B of the HDD 136 in association with the display positions (objects to be displayed: PD, right eye's spherical power, left eye's cylindrical power, and the like) of the display contents (S12).

Subsequently, the display control portion 135d of the CPU 135 displays the respective display contents acquired by the display content acquisition portion 135c on the monitor portion 131 of the computer device 130 in the predetermined format (S13).

Note that, when the optometer 1 is connected to the electronic medical chart system, the display contents are transmitted to a server or the like of the system concerned. This server or the like automatically writes down the display contents in the electronic medical chart of the subject 300.

[Function and Effect]

According to the optometer 1 of this embodiment as described above, the PD, the correcting refractive power, and the like, which are mechanically displayed by the manual-type phoropter 120, are automatically displayed on the monitor portion 131 of the computer device 130. Accordingly, it is not necessary to visually read the examination result displayed on the phoropter 120, or to manually record the examination result in the computer device 130 or the recording sheet. Hence, even in the case of performing the optometry by using the manual-type phoropter that mechanically displays the examination result, it becomes possible to record the examination result without making an error.

In such a way, a situation is avoided where a misdiagnosis is caused by erroneous recording contents, and burdens on the examiner and the subject owing to a reexamination are eliminated. Further, a burden on the examiner, which has been conventionally regarded as a problem and is caused by manual recording processing of the examination results, is eliminated or reduced.

[Various Modified Examples]

Various modified examples of the optometer as described above are described.

(Application to Trial Frame)

The structure of the present invention is also applicable to an optometer to which the trial frame is applied, into which the plural trial lenses are selectively attachable as the refractive power correcting means for imparting the correcting spherical powers to the eyes to be examined.

Figure 16A:
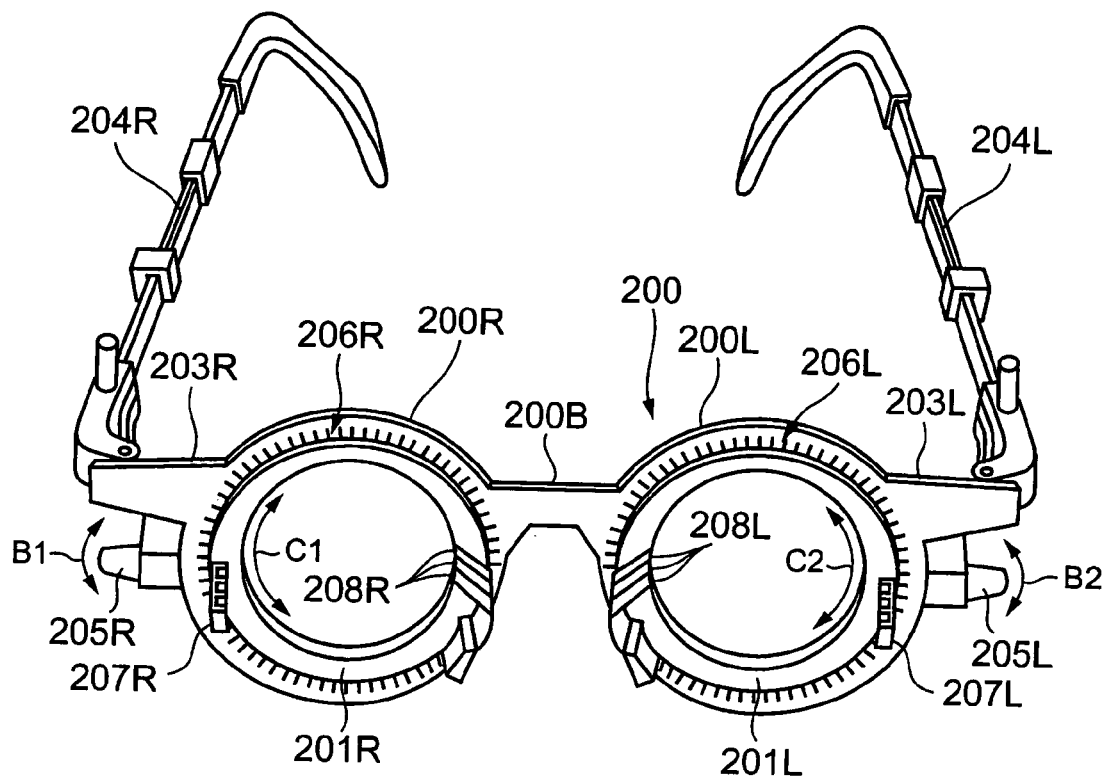
Figure 16B:
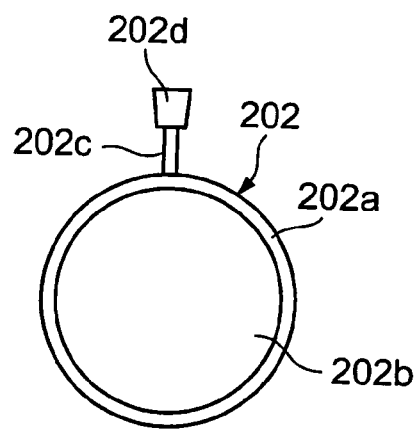

As shown in FIG. 16, on a trial lens 202 selectively attached into a trial frame 200, a tab 202d indicating refractive power (spherical power, cylindrical power, and the like) of a lens 202b is provided. The trial lens 202 (in particular, one for adding the cylindrical power) is set to be rotatable in a state of being attached into the trial frame 200.

On a front face of the trial frame 200, scales 206L and 206R are provided. The cylindrical axis degree of the trial lens 202 for imparting the cylindrical power is displayed in such a manner that the tab 202d (protrusion 202c) indicates the scales 206L and 206R.

Note that the tab 202d (protrusion 202c) of each trial lens 202 and the scales 206L and 206R of the trial frame 200 are structured to mechanically display the examination results, and form the "examination result display mechanism" of the present invention.

The subject is located at the position shown in FIG. 9, and the trial frame 200 is put on the subject. In a similar way to the examination by the phoropter, the examiner selectively attaches the trial lens 202 into the trial frame 200 while presenting the various targets C by the optotype device 140, and finds the correcting refractive power that satisfies the subject. At this time, a spherical lens with the correcting spherical power, a cylindrical lens with the correcting cylindrical power, a prism lens with the prism power, or the like, each of which satisfies the subject, is attached into the trial frame 200. Further, the tab 202d of the cylindrical lens is located so as to indicate the direction of the cylindrical axis degree, and the tab 202d of the prism lens is located so as to indicate the direction of the prism base.

Note that, as in the conventional case, a plurality of the trial lenses 202 can be attached simultaneously into the trial frame 200. Further, each trial lens 202 is attached into the trial frame 200 so that the value of the refractive power of the lens 202b, which is represented on the tab 202d, can be directed to the imaging device 2 side.

The examiner operates the computer device 130, and so on, thereby taking an image including the tab 202d of each trial lens 202 by the imaging device 2. Image data of the image is transmitted to the computer device 130 through the cable 3.

The CPU 135 of the computer device 130 analyzes the image thus taken, and acquires a numeric value represented on the tab 202d of each trial lens 202, cylindrical axis degrees represented on the scales 206L and 206R indicated by the tab 202d (protrusion 202c), and the like. Such acquisition processing can be performed by a technique according to pattern recognition of shapes of numeric values, characters, and marks, and by a technique for detecting positions of indication marks and the like as in the above-described embodiment.

Further, the CPU 135 displays the acquired numeric values and the like on the monitor portion 131 in a predetermined format (for example, list format as in the above-described embodiment).

According to the optometer as described above, even in the case of performing the optometry by using the trial frame and the trial lenses, which are structured to mechanically display the examination results, it becomes unnecessary to visually read and record the examination results of the optometry, which makes it possible to avoid a recording error.

(Coping with Case where Display Content in Taken Image Has Been Unacquired)

This modified example is one for suitably coping with such a case where the display contents in the taken image of the phoropter or the like have been unacquirable in the above-described respective structures according to the present invention.

The optometer according to the present invention includes the structure to image the manual-type phoropter, the trial frame, or the like, to analyze the image thus taken, and to acquire and display the display contents (examination results) of the phoropter or the like. However, such a case possibly occurs that a clear image cannot be taken owing to lightness in an examination room, and so on, and the display contents of the phoropter or the like cannot be thereby acquired surely. Note that, though it is conceived that such a situation can be avoided if employing a sufficiently high-quality and high-sensitivity one as the imaging element 23 of the imaging device 2, it is desirable to include a structure according to this modified example in consideration that the optometer is used under various environments.

Figure 10:
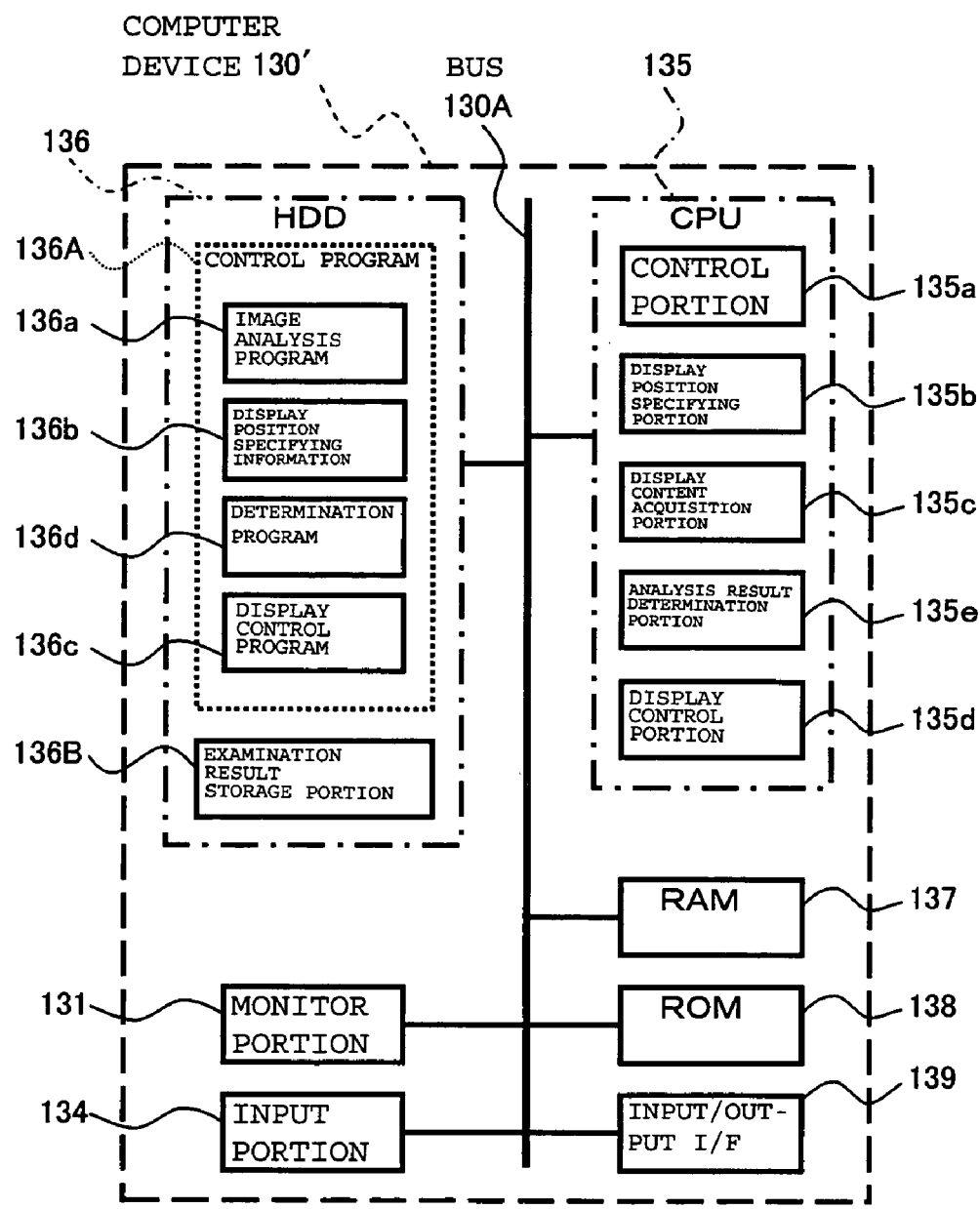
FIG. 10 is a block diagram showing a schematic structure of a computer device included in an optometer according to a modified example of the embodiment of the present invention.

FIG. 10 shows an example of a computer device included in an optometer according to this modified example. A computer device 130' shown in this drawing is a modified example of the computer device 130 of the above-described embodiment, which is shown in FIG. 1, in which similar constituents to those of the computer device 130 are denoted by the same reference symbols.

In addition to the similar constituents to those of the above-mentioned computer device 130, the computer device 130' includes a determination program 136d in the control program 136A of the HDD 136. The CPU 135 operates as an analysis result determination portion 135e by executing the determination program 136d.

The analysis result determination portion 135e performs processing of determining whether or not the positions of all the display portions of the phoropter 120 in the taken image have been specified in the processing by the display position specifying portion 135b. A list of the display portions to be specified is stored in the determination program 136d, and the analysis result determination portion 135e compares the respective display portions specified by the display position specifying portion 135b with the list, thereby determining the existence of a specification. Note that, in the case of making it possible to select the display portions to be specified, that is, in the case of structuring the analysis result determination portion 135e to be capable of selecting the objects (PD, spherical power, and the like) to be acquired from the taken image and to be displayed on the monitor portion 131, the analysis result determination portion 135e determines whether or not the display positions of the selected objects on the phoropter 120 have been specified entirely.

When the analysis result determination portion 135e determines that there is a display portion whose position is not specified, the display control portion 135d displays, on the monitor portion 131, a message to the effect or a message explicitly indicating the unspecified display portion, for example, a message saying "Display position cannot be specified" or "Display position of spherical power of left eye cannot be specified".

In addition to or in place of the processing as described above, the analysis result determination portion 135e performs processing for determining whether or not all the display contents on the display portions of the phoropter 120 in the taken image have been acquired in the processing by the display content acquisition portion 135c. Also in this case, the list of the display contents to be acquired is stored in the determination program 136d, and the analysis result determination portion 135e compares the display contents acquired by the display content acquisition portion 135c with the list, and determines the existence of the acquisition. Note that, in the case of structuring the analysis result determination portion 135e to be capable of selecting the display contents to be acquired, the analysis result determination portion 135e determines whether or not all the selected display contents have been acquired.

When the analysis result determination portion 135e determines that there is an unacquired display content, the display control portion 135d displays, on the monitor portion 131, a message to the effect or a message explicitly indicating the unacquired display content, for example, a message saying "Display content cannot be acquired" or "Spherical power of left eye cannot be acquired".

According to this modified example, a notice can be issued that the examination results displayed on the phoropter 120 are not acquired effectively. Hence, in order to acquire the examination results effectively, the examiner can takes measures such as retaking the image of the phoropter 120 and visually confirming the display portions of the phoropter 120. In such a way, a recording error owing to the nonexistence of the acquisition of the examination results will be avoided.

Note that, as contents of the notice (message and the like), contents of the measures may also be displayed, such as "Confirm the display of phoropter and make an entry". Further, it is possible to use not only the above-described visual method but also an auditory method using a voice message, a beep sound, and the like, as a notifying method. Further, it is obvious that the structure of this modified example is also applicable to the examination using the trial frame 200.

(Imaging Mode by Imaging Device)

Although the above-described embodiment is structured so as to image the entire image of the front face 120F of the phoropter 120 at one time, it is also possible to constitute the embodiment so as to take a part of the image. For example, a structure can be made so as to individually image the right measurement unit 120R and left measurement unit 120L of the phoropter 120, and to individually image the respective display portions of the phoropter 120. Further, a structure may also be made so as to collectively image a plurality of the display portions arranged adjacent to one another.

In this case, changing means for changing an imaging position of the front face 120F of the phoropter 120 is provided in the imaging device 2, and the change of the imaging position by the changing means is controlled by the control portion 21. At this time, the control portion 21 performs the control processing based on a control signal from the control portion 135a of the computer device 130.

As the above-described changing means, for example, usable are a drive device (stepping motor and the like) for rolling the imaging device 2 or the imaging optical system 22 itself, and a structure to displace the imaging direction by providing a prism in the imaging optical system 22.

In the case of employing the structure of this modified example, a zoom image may also be taken by controlling the above-mentioned variable power lens of the imaging optical system 22. In such a way, an enlarged image of the display contents of the display portions of the phoropter 120 can be obtained. Accordingly, it becomes possible to perform the display position specifying processing and the display content acquisition processing by the computer device 130 more surely.

Further, in the case of employing the structure of this modified example, an imaging order of the respective portions of the phoropter 120 can be predetermined. In the case of performing the individual measurements for the right measurement unit 120R and the left measurement unit 120L, for example, the changing means is controlled so that the PD display portion 122 can be imaged first, the right measurement unit 120R can be imaged next, and the left measurement unit 120L can be imaged finally (Case 1). Further, in the case of individually imaging the respective display portions of the phoropter 120, the changing means is controlled so that the respective display portions can be imaged in order of, for example, the PD display portion 122, the right spherical power display portion 161R, the right cylindrical power display portion 162R, the right cylinder axis display portion 164R, the right rotary prism portion 155R, the left spherical power display portion 161L, the left cylindrical power display portion 162L, the left cylindrical axis display portion 164L, and the left rotary prism portion 155L (Case 2).

The imaging order as described above is predetermined, the imaging order is prestored in the computer device 130, and the processing by the display position specifying portion 135b and the display content acquisition portion 135c is performed according to the imaging order. Then, it becomes possible to accurately perform those pieces of processing. The reason is as follows. Specifically, an improvement of processing accuracy is expected in the case of specifying the display portions in the taken images each including a small number of the display portions (one, four, and four in the above-described Case 1, and one per each image in the above-described Case 2) and of acquiring the display contents rather than in the case of specifying the respective display portions of the taken image including a large number of the display portions (nine in the above-described embodiment) and of acquiring the display contents.

(Numeric Value, Indication Mark, and the Like of Display Portions and the Like of Phoropter)

The numeric values, the scales, the indication marks, and the like, which are provided on the display portions and the like of the phoropter 120 by inscription and so on, may be formed of ink and paint of a color within a wavelength range in which a photosensitivity of the imaging element 23 of the imaging device 2 is high, thereby making it possible to acquire a more clear taken image. Further, the numeric values and the like may be formed of ink and paint of a special color such as a fluorescent color.

As a second modified example regarding the numeric values, indication marks, and the like of the display portions and the like, a structure is also possible, in which the respective display portions are colored with different colors, and spectrum of the taken image are analyzed by the CPU 135 of the computer device 130, thereby acquiring the display contents of the respective display portions based on differences of the colors.

Further, the display mode of the display portions is not limited to the numeric values, the characters, the marks, and the like as in the above-described embodiment, and it is satisfactory if the structure to mechanically display the examination results is provided.

(Storage and Utilization of Acquired Examination Results)

The display contents (examination results) of the respective display portions, which are acquired by the CPU 135 of the computer device 130, are stored in the examination result storage portion 136B and displayed on the monitor portion 131 in the above-described embodiment. However, the present invention is not limited to this. For example, a structure only for storing the display contents in the examination result storage portion 136B, a structure only for displaying the display contents on the monitor portion 131 without storing the same, or the like can be employed.

Further, a structure can be made so as to transmit the acquired examination results to the electronic medical chart management system when the optometer is connected to the system. For example, the examination results are automatically written down in the electronic medical chart of the subject by the electronic medical chart management system. In such a way, labor of manually entering the examination results to the electronic medical chart can be saved, and an occurrence of an erroneous input can be avoided.

Further, a structure can be made so as to connect the optometer to a lens grinder (or control device thereof) for forming and processing, by grinding, a lens of eyeglasses put on by the subject, and to transmit the examination results by the optometer to the lens grinder (or control device thereof). The lens grinder processes the lens of the eyeglasses put on by the subject based on the examination results. In such a way, labor of entering the examination results to the lens grinder (or control device thereof) can be saved, and the occurrence of the erroneous input can be avoided.

(Others)

The structure described above in detail is only an example for embodying the optometer according to the present invention. Hence, it is possible to make arbitrary modifications within the scope of the gist of the present invention.

For example, in the case of performing, by the single computer device, processing for examination results by a plurality of the subjective optometers (phoropters or trial frames), a structure can be made so as to prestore data of positions of the respective display portions of the respective subjective optometers as the display position specifying information 136b, and to provide selecting means (input portion 134 of computer device 130, or the like) for selecting the subjective optometer for use in the examination, thereby executing the display position specifying processing and the display content acquisition processing by using the display position specifying information 136b corresponding to the selected optometer.

Further, a structure may also be made so as to provide examination distance selecting means (input portion 134 of computer device 130, or the like) for selecting a distance (3 meters, 5 meters, or the like) between the subjective optometer and the optotype device, and to automatically change a focus distance, an imaging magnification, and the like of the imaging device 2 in response to the distance thus selected. For example, such changing processing is controlled by the control portion 21 of the imaging device 2 in response to a control signal from the control portion 135a of the computer device 130.

Further, it is also possible to make a structure so as to provide a predetermined reference mark on the front face 120F of the phoropter 120, and to store relative positions of the respective display portions to the reference mark as the display position specifying information 136b, thereby specifying the positions of the respective display portions based on the relative positions.

Further, the optometer according to the present invention can also acquire measurement values other than the spherical power, the cylindrical power, the cylindrical axis degree, the prism power, and the PD as required. Alternatively, the optometer may selectively acquire any of various measurement values including them. A selecting operation for them is performed by the input portion 134 of the computer device 130, or the like.

Further, the structure according to the present invention is applicable not only to the subjective optometer such as the phoropter and the trial frame which are as described above but also to an arbitrary optometer including the structure to mechanically display optical characteristic values such as the refractive powers of the eyes to be examined and measurement values such as the PD therebetween.

What is claimed is:

1. An optometer, comprising:
an examination result display mechanism comprising a phoropter configured to mechanically display a numeric value specifying a correcting refractive power for an eye to be examined;
imaging part configured to take an image of at least a numeric part shown on a face of the examination result display mechanism;
image analysis part configured to recognize a shape of a pattern included in the image of the numeric part taken by the imaging part to identify the numeric value indicated by the shape of the pattern to acquire the parameter in accordance with the numeric value; and
an electric display part configured to electrically display on screen the parameter acquired by the image analysis part.

2. An optometer according to claim 1, further comprising:
target presentation part configured to present a target to the eye to be examined; and
refractive power correcting part disposed to oppose the target presentation part and configured to impart, to the eye to be examined to which the target is presented, at least one of spherical powers and cylindrical powers with various frequencies for correcting a refractive power of the eye to be examined,
wherein the examination result display mechanism is provided to the refractive power correcting part, and displays the at least one of a spherical power and a cylindrical power imparted to the eye to be examined by numeric values, and
wherein image analysis part acquires as the parameter a spherical power and/or a cylindrical power.

3. An optometer according to claim 1, wherein:
the imaging part includes an imaging element configured to detect imaging light and to convert the imaging light into an electric signal; and
the numeric values displayed by the examination result display mechanism are formed of a color within a wavelength in which a photosensitivity of the imaging element is high.

4. An optometer according to claim 2, wherein:
the imaging part includes an imaging element configured to detect imaging light and to convert the imaging light into an electric signal; and
the numeric values displayed by the examination result display mechanism are formed of a color within a wavelength in which a photosensitivity of the imaging element is high.

5. An optometer according to claim 1, wherein:
the examination result display mechanism includes a scale representing a measurement range in an examination relating to the examination result, and an indication mark indicating a position on the scale, the position corresponding to the examination result; and
the image analysis part detects the indication mark in the image taken by the imaging part, and acquires the parameter based on the position on the scale indicated by the indication mark.

6. An optometer according to claim 5, further comprising:
target presentation part configured to present a target to the eye to be examined; and
refractive power correcting part disposed to oppose the target presentation part and configured to impart, to the eye to be examined to which the target is presented, at least one of spherical powers and cylindrical powers with various frequencies for correcting a refractive power of the eye to be examined,
the examination result display mechanism is provided to the refractive power correcting part; and
the scale represents a measurement range of at least one of a cylindrical axis degree of a cylindrical power and a prism power imparted to the eye to be examined,
wherein the image analysis part acquires as the parameter a spherical power and/or a cylindrical power.

7. An optometer according to claim 5, wherein the scale represents a measurement range of an inter-pupil distance of the eye to be examined.

8. An optometer according to claim 5, wherein:
the imaging part includes an imaging element configured to detect imaging light and to convert the imaging light into an electric signal; and
at least one of the scale and the indication mark is formed of a color within a wavelength in which a photosensitivity of the imaging element is high.

9. An optometer according to claim 6, wherein:
the imaging part includes an imaging element configured to detect imaging light and to convert the imaging light into an electric signal; and
at least one of the scale and the indication mark is formed of a color within a wavelength in which a photosensitivity of the imaging element is high.

10. An optometer according to claim 7, wherein:

the imaging part includes an imaging element configured to detect imaging light and to convert the imaging light into an electric signal; and at least one of the scale and the indication mark is formed of a color within a wavelength in which a photosensitivity of the imaging element is high.

11. An optometer according to claim 2, wherein:

the refractive power correcting part is a phoropter incorporating plural correcting lenses therein, and for disposing the plural correcting lenses in a switching manner immediately in front of the eye to be examined; and the examination result display mechanism is provided to a front face of the phoropter.

12. An optometer according to claim 6, wherein:

the refractive power correcting part is a phoropter incorporating plural correcting lenses therein, and for disposing the plural correcting lenses in a switching manner immediately in front of the eye to be examined; and the examination result display mechanism is provided to a front face of the phoropter.

13. An optometer according to claim 2, wherein:

the refractive power correcting part includes plural trial lenses having correcting lenses and tabs displaying refractive powers of the correcting lenses, and a trial frame into which the plural trial lenses are selectively attachable; and the examination result display mechanism includes the tabs of the trial lenses.

14. An optometer according to claim 6, wherein:

the refractive power correcting part includes plural trial lenses having correcting lenses and tabs displaying refractive powers of the correcting lenses, and a trial frame into which the plural trial lenses are selectively attachable; and the examination result display mechanism includes the tabs of the trial lenses.

* * * * *